United States Patent [19]

Kerr et al.

[11] Patent Number: 5,075,079
[45] Date of Patent: Dec. 24, 1991

[54] SLIDE ANALYSIS SYSTEM

[75] Inventors: Alexander F. Kerr, Yorktown; Edwin H. Mernyk, Tarrytown, both of N.Y.; George E. Zabetakis, Bethel, Conn.; Uri Escoli, Teaneck, N.J.

[73] Assignee: Technicon Instruments Corporation, Tarrytown, N.Y.

[21] Appl. No.: 526,270

[22] Filed: May 21, 1990

[51] Int. Cl.⁵ .................. G01N 35/04; G01N 35/06
[52] U.S. Cl. ....................... 422/64; 422/65; 422/68.1; 436/47; 436/49
[58] Field of Search ............... 422/63, 64, 65, 67, 422/68.1; 436/43, 45, 47, 49; 73/863.11, 864.21

[56] References Cited

U.S. PATENT DOCUMENTS

| | | | |
|---|---|---|---|
| 4,142,863 | 3/1979 | Covington et al. | 422/63 |
| 4,279,861 | 7/1981 | Jessop | 422/67 |
| 4,296,069 | 10/1981 | Smith et al. | 422/65 |
| 4,296,070 | 10/1981 | Montalto et al. | 422/65 |
| 4,298,571 | 11/1981 | Di Fulvio et al | 422/65 |
| 4,452,899 | 6/1984 | Alston | 422/63 |
| 4,512,952 | 4/1985 | Blanding et al. | 422/64 |
| 4,568,519 | 2/1986 | Hamilton et al. | 422/67 |
| 4,656,006 | 4/1987 | Assmann et al. | 422/65 |
| 4,670,219 | 6/1987 | Nelson et al. | 422/65 |
| 4,696,902 | 9/1987 | Bisconte | 435/300 |
| 4,708,886 | 11/1987 | Nelson | 422/64 |
| 4,780,283 | 10/1988 | Meinecke et al. | 422/58 |
| 4,812,392 | 3/1989 | Miyake et al. | 435/289 |
| 4,855,109 | 8/1989 | Muraishi et al. | 422/63 |
| 4,948,737 | 8/1990 | Quenin et al. | 422/63 |

*Primary Examiner*—David L. Lacey
*Assistant Examiner*—Kimberly A. Trautman
*Attorney, Agent, or Firm*—Jeffrey M. Greenman

[57] ABSTRACT

The slide analysis system includes a slide holding module spaced from an incubator module. A slide transfer device or pick and place mechanism withdraws slides from the slide holding module and inserts them into the incubator module. A metering device deposits serum onto a slide that is held in a spotting position by the slide transfer device. The metering device is movable to a sampling position in the slide holding module to aspirate serum from a serum source on the slide cartridge in the slide holding module and is also movable to a spotting position to spot serum on the slide held by the slide transfer device. The slide transfer device has rotational as well as transverse movement and includes jaws for gripping onto the sides of slides to withdraw a single slide from a cartridge, transport it to the incubator, insert the slide in the incubator and thereafter remove it from the incubator. The metering device also has rotational as well as elevational movement and includes a built-in pipette tip ejector for discarding a used pipette tip.

17 Claims, 24 Drawing Sheets

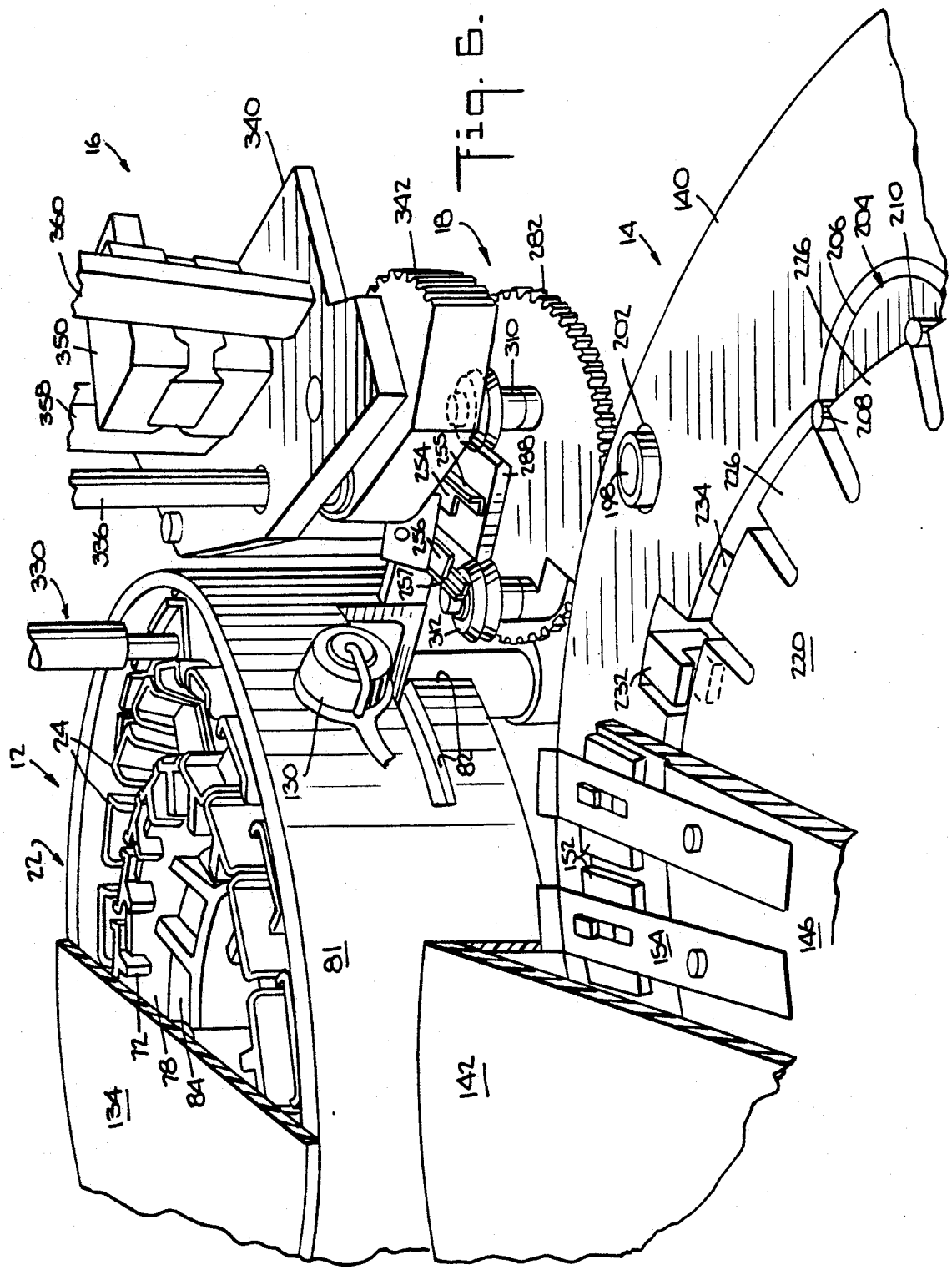

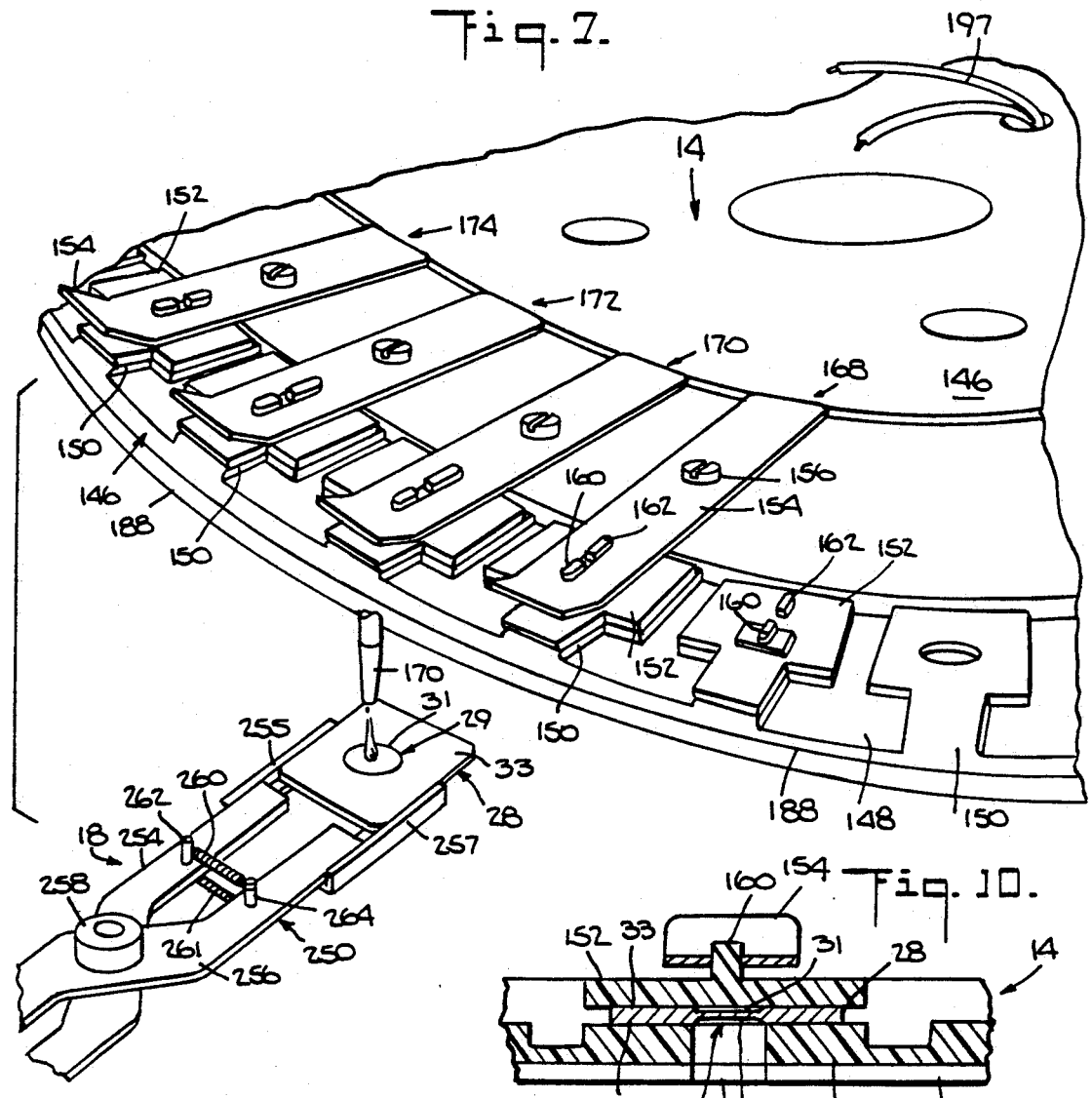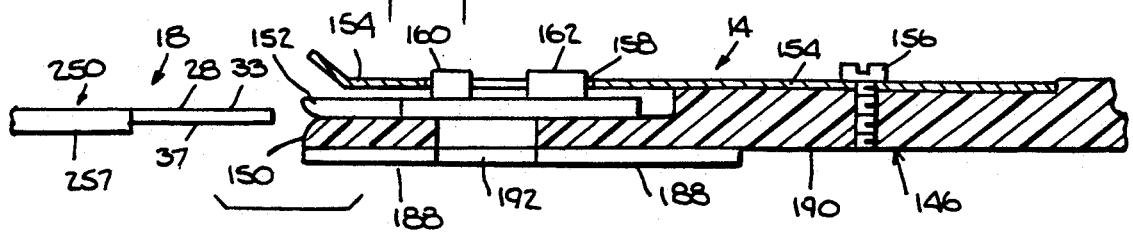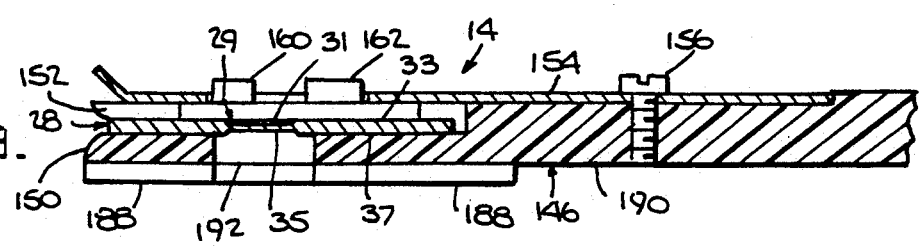

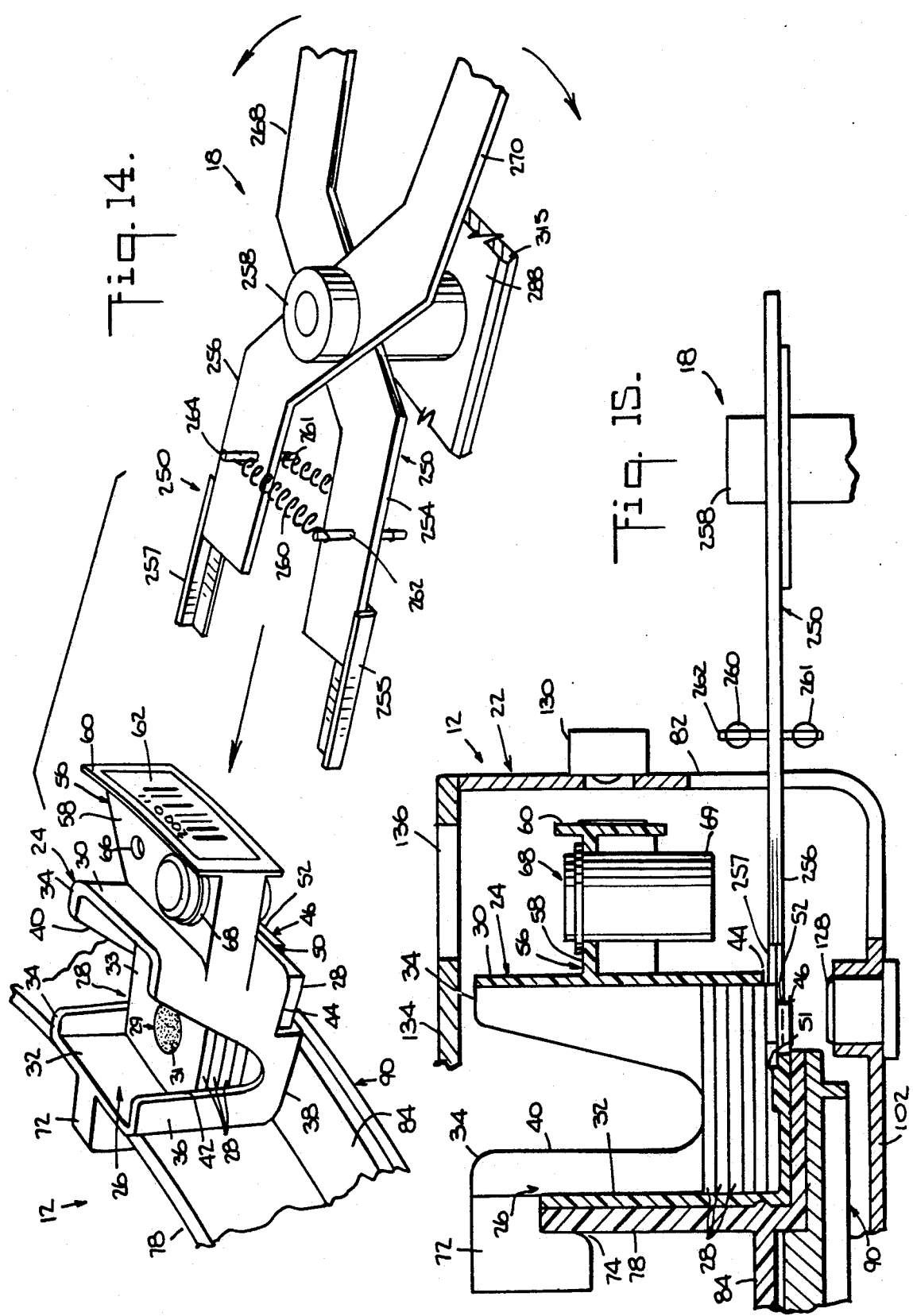

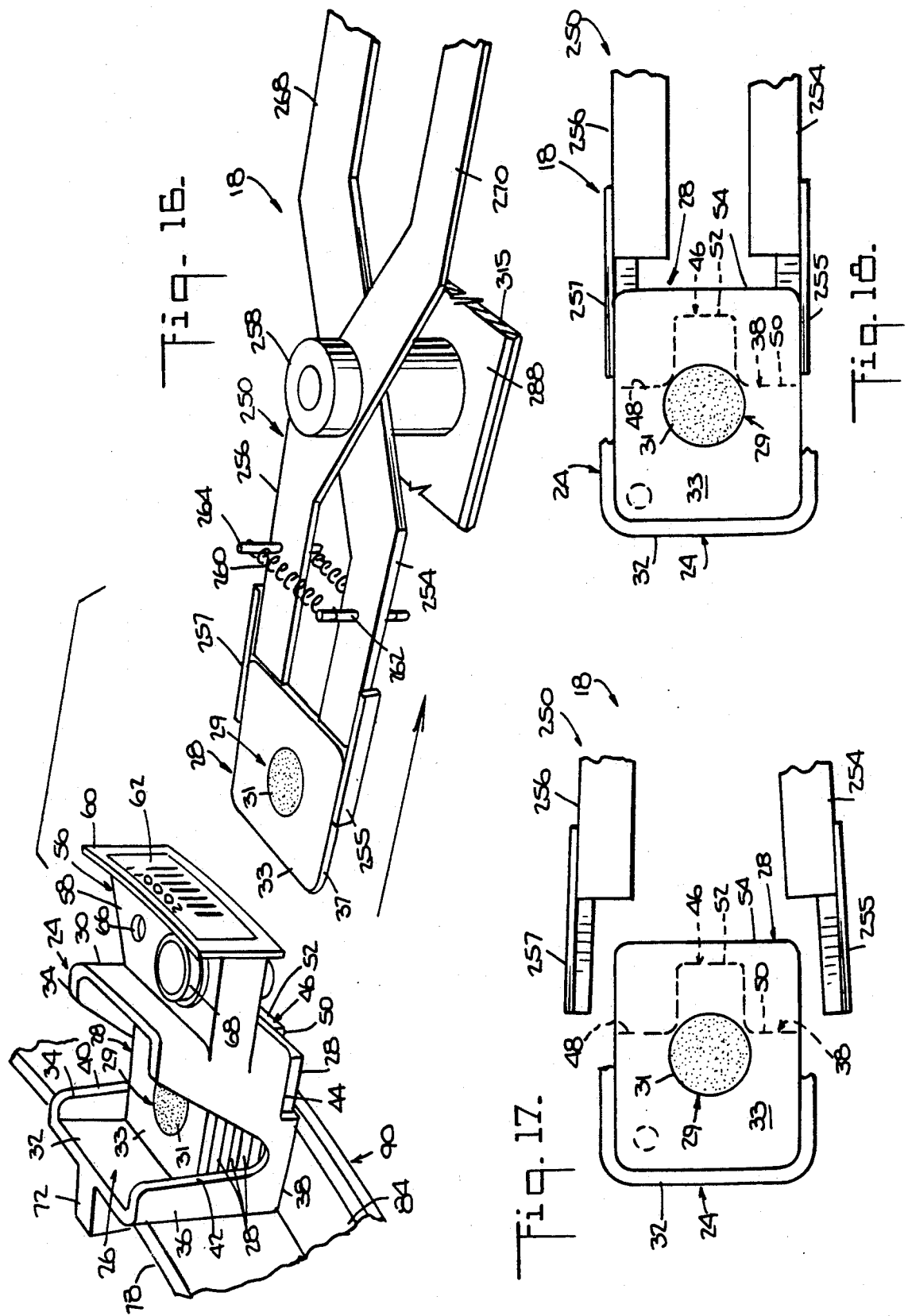

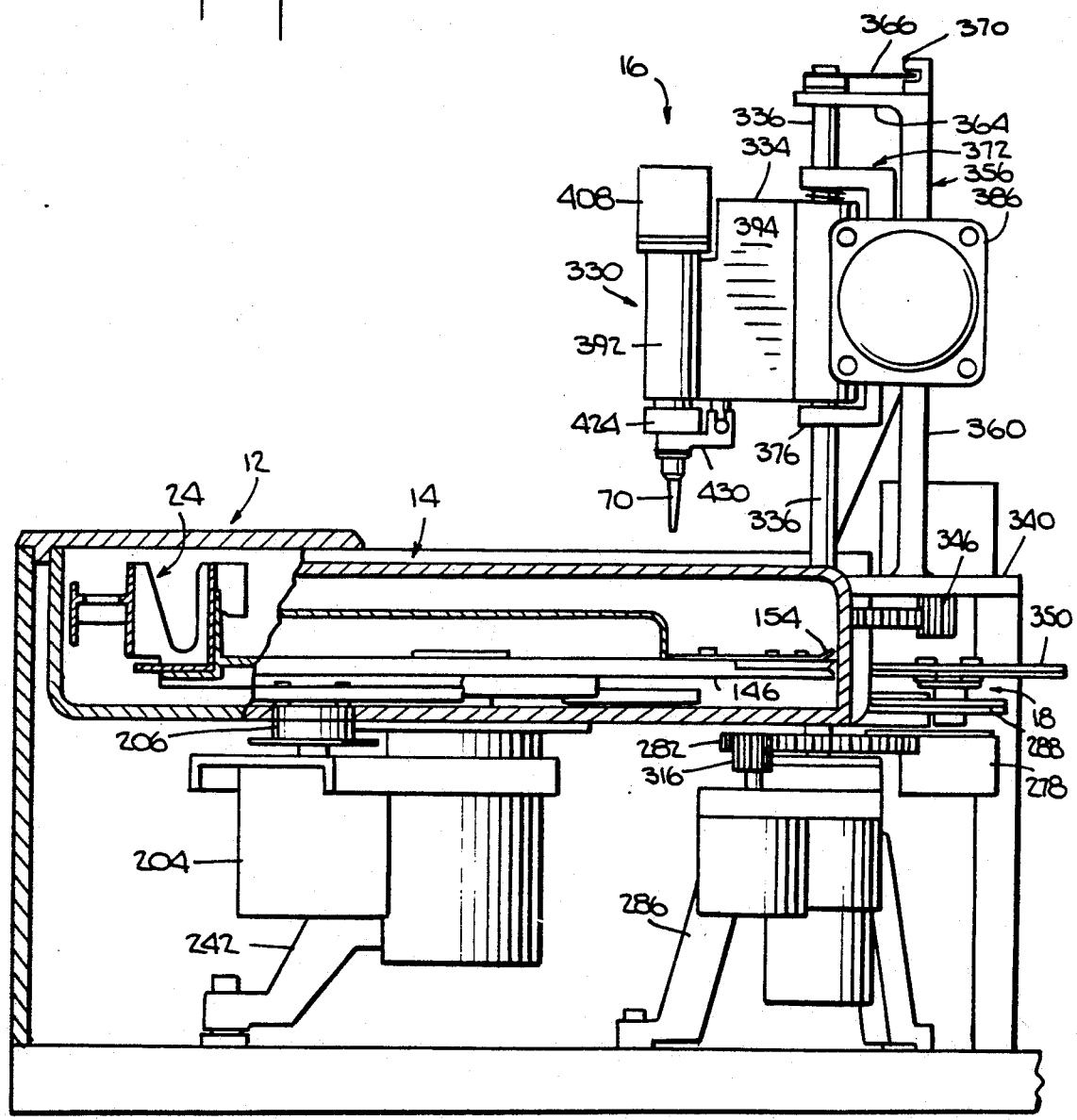

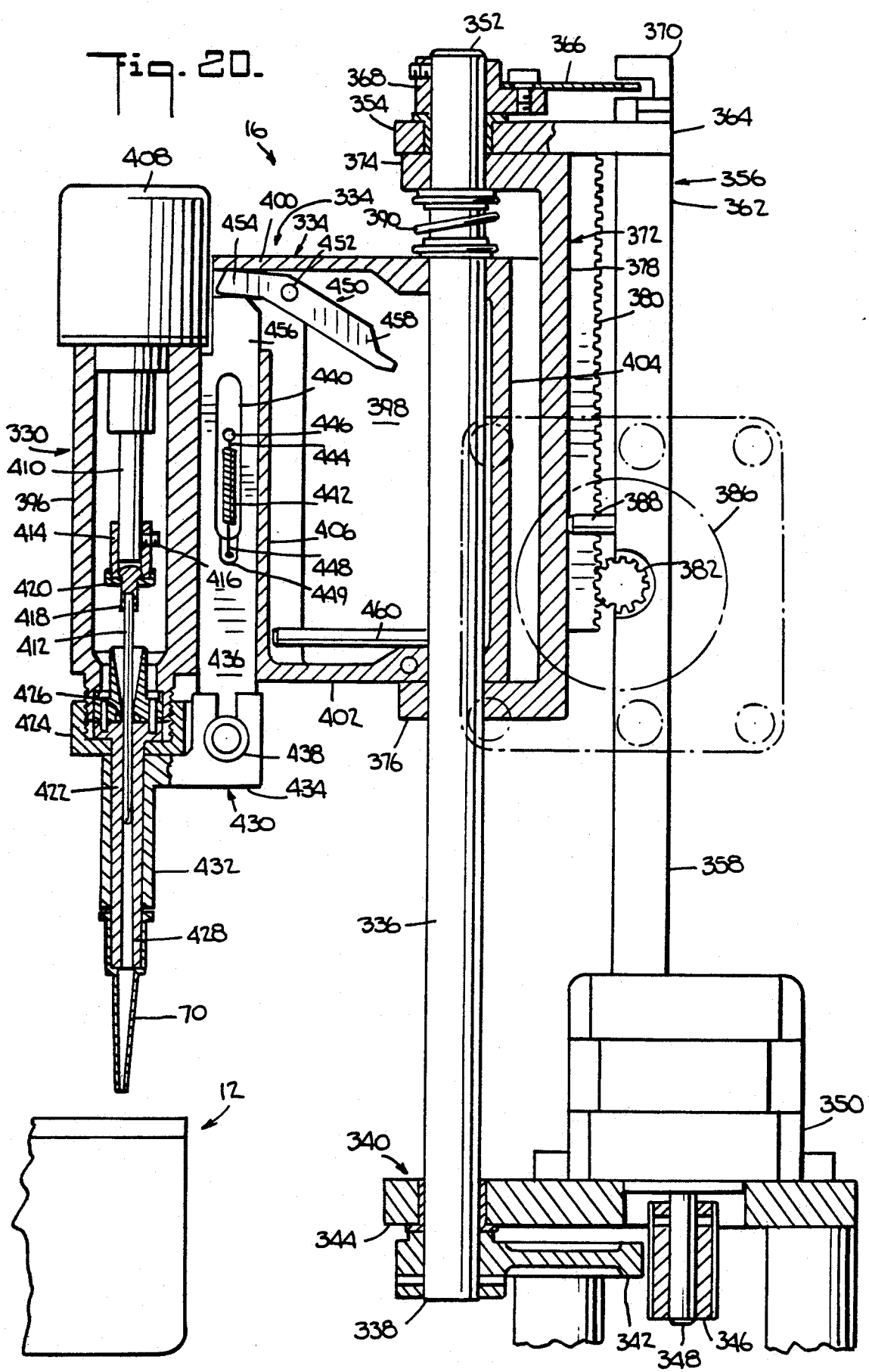

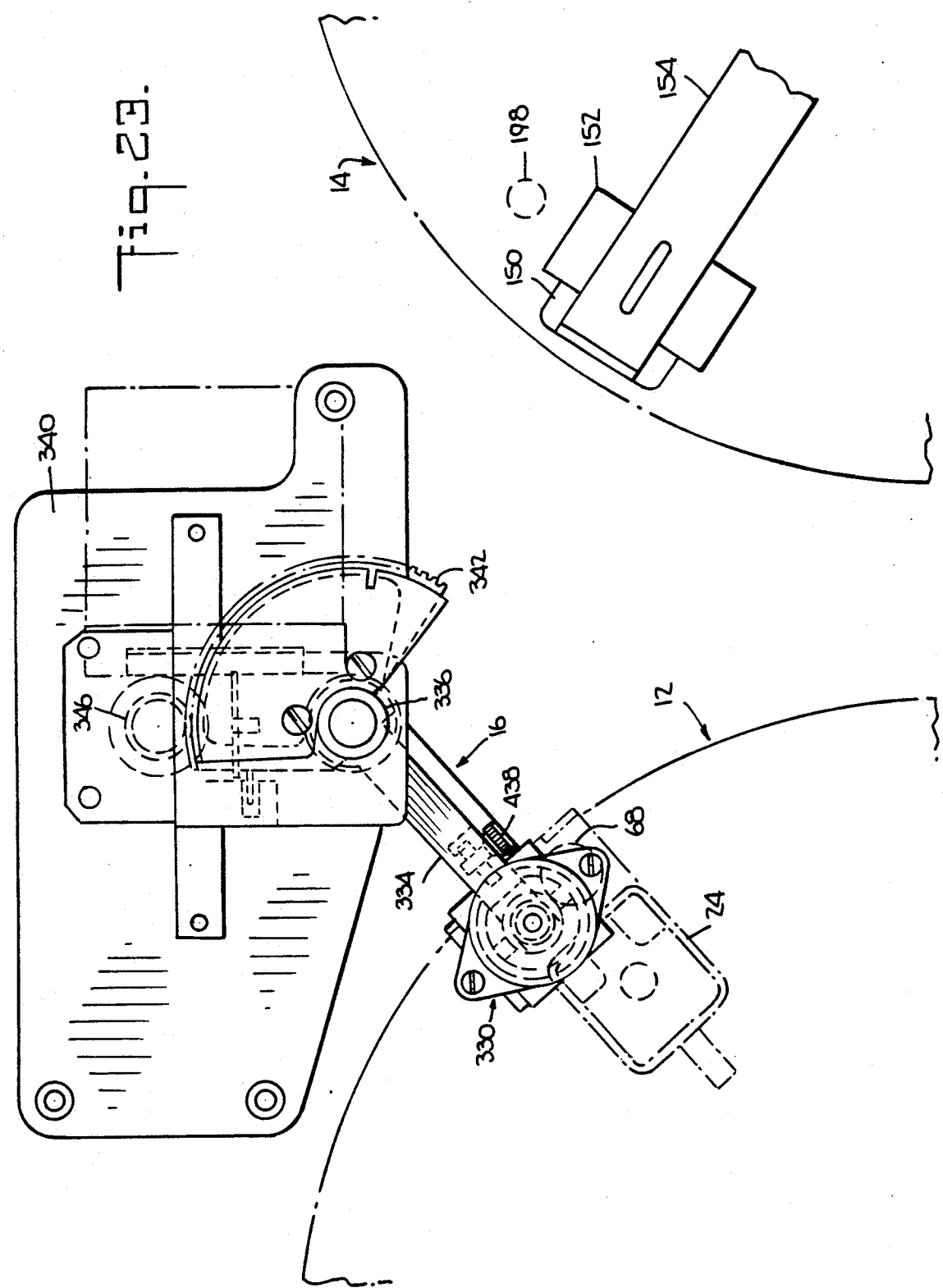

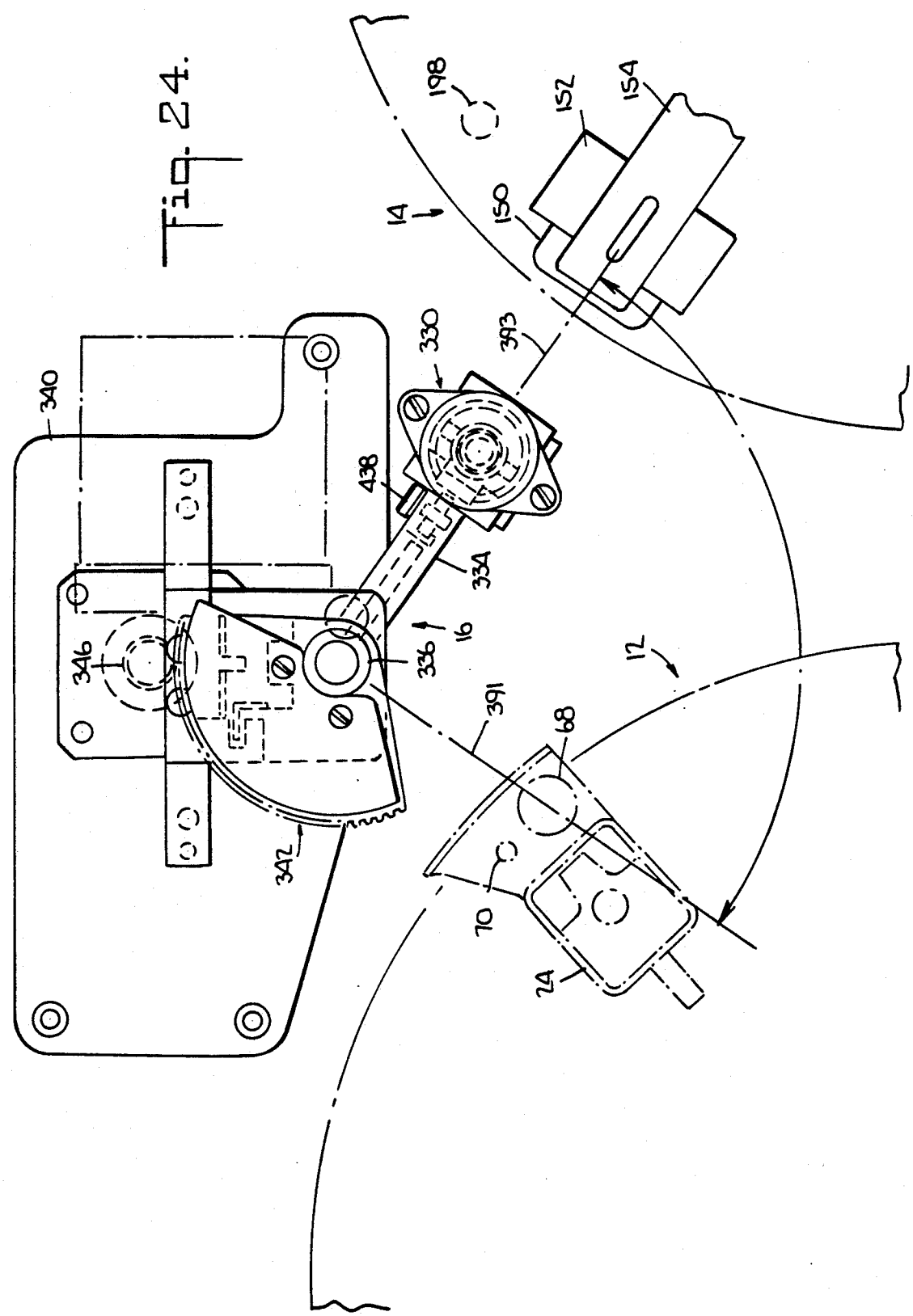

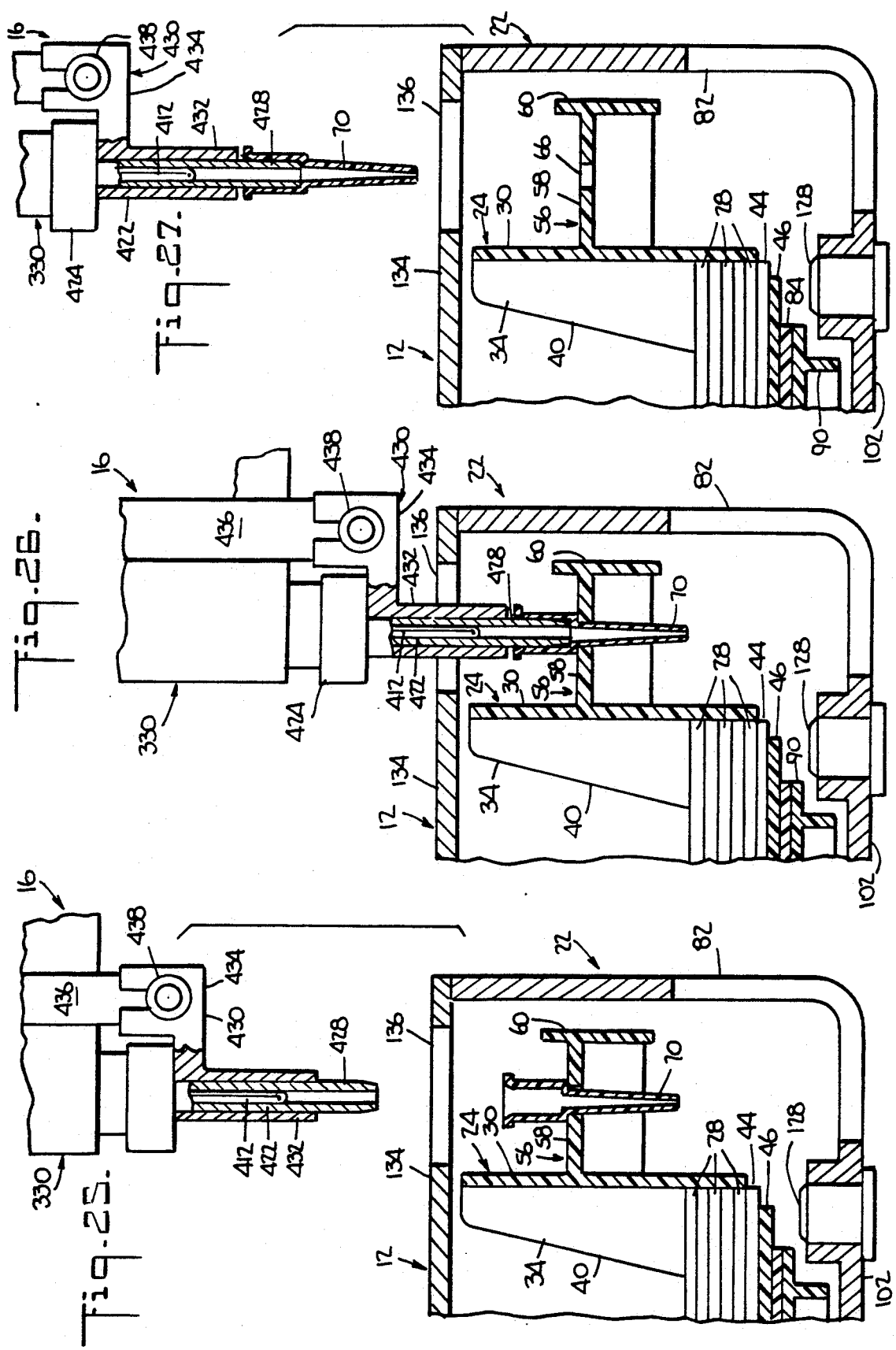

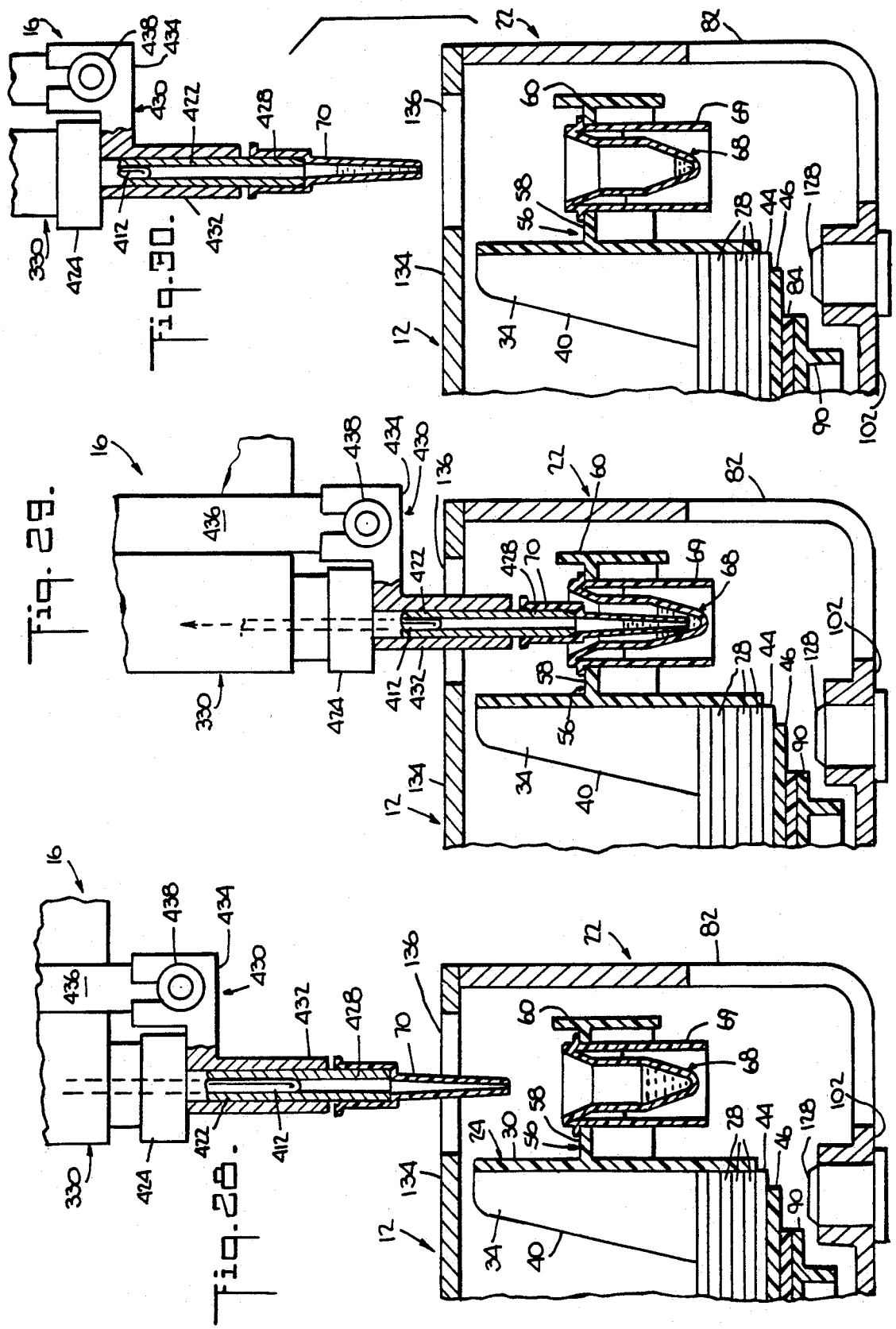

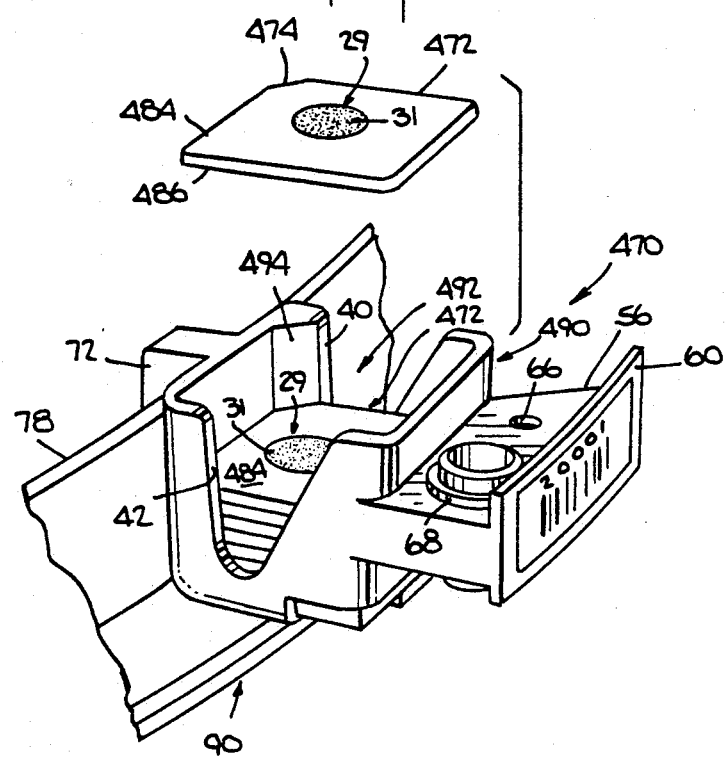
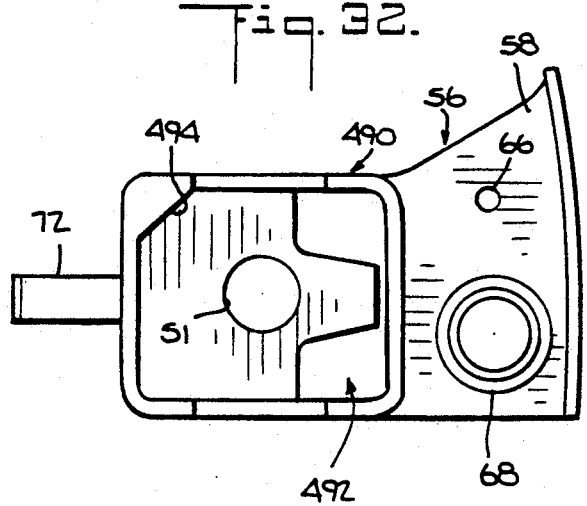
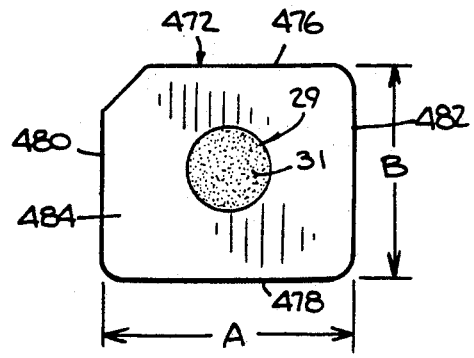

SLIDE ANALYSIS SYSTEM

BACKGROUND OF THE INVENTION

This invention relates to systems for automatic analysis of slides spotted with biological fluids such as blood and more particularly to a slide analysis system having novel slide transfer and liquid sample dispensing components for spotting a slide.

The analysis of biological fluid samples such as blood to help evaluate the health or well being of an individual is often carried out in test laboratories specially set up for fluid sample testing purposes. Thus, a blood sample that is withdrawn from a patient in a physician's office may be packed and shipped to a test facility, unless the physician's office is equipped with analytical apparatus for performing the desired tests. However in most cases, physicians' offices are not set up to perform detailed analyses of blood samples.

Thus an outside test facility performs selected tests on the blood sample, documenting the results in a report that is sent to the physician. A time lapse of several days or more may occur between blood sample procurement by the physician and the physician's receipt of the test report from the testing laboratory. In many instances such a delay can be crucial in the treatment of the patient's illness.

Timing is especially critical if a patient has an existing or emerging deleterious condition which is only detectable from a blood test and requires immediate treatment.

The sheer volume of blood testing that is carried out in laboratories or test facilities usually dictates the amount of time delay that will occur between receipt of a blood sample and the forwarding of a corresponding report to a physician. As more and more individuals request blood tests, there is the prospect of prolonged delays between sample procurement by a physician and the reporting of test results from test laboratories.

In response to the increasing demand for blood tests and the need for shorter turnaround times in reporting the test results, there has been a progressive development of apparatus for analyzing biological fluid samples. Such apparatus can process samples in relatively short periods of time and are relatively simple to operate. Some known apparatus typically perform diverse automatic analyses of fluid samples after such samples have been deposited on slides.

For example, U.S. Pat. Nos. 4,568,519; 4,512,952; 4,296,069 and 4,296,070 disclose systems and system components for automatic analysis of blood samples deposited on slides. The disclosed systems require a first slide transfer mechanism for moving slides relative to a slide supply device, a second slide transport device for transporting the slides to a metering device which spots the slides with the fluid sample, and a third slide transfer device for moving the spotted slides relative to an incubator device. The slide transfer mechanisms can include slide ejecting devices and slide feed devices for moving a slide from one location to another. Due to the intricacy, size requirements and expense of the systems disclosed in the foregoing patents, their use is warranted primarily in laboratories and specialized test facilities rather than a physician's office.

U.S. Pat. Nos. 4,452,899 and 4,675,301 show a metering head that automatically moves up and down as well as back and forth and carries a disposable pipette tip. An ejection device for removing the pipette tip from the metering device is spaced and separate from the metering head. Thus the ejection device is not built into the metering head and the metering head must be brought into alignment with the ejection device in order to eject the pipette tip.

It is thus desirable to provide a slide analysis system having a single multi-function slide transfer device for moving individual slides to several locations and a slide spotting device which accesses blood samples in a slide holding device, spots the slides with the accessed sample and has a built-in pipette tip ejector for automatically ejecting a used pipette tip when the testing of an individual fluid sample is completed.

It is further desirable to provide an automatic slide analysis system which is sufficiently compact to be utilized in a physician's office or a small laboratory and thus helps obviate the need by physicians or small laboratories to resort to specialized test facilities for all blood sample analyses.

OBJECTS AND SUMMARY OF THE INVENTION

Among the several objects of the invention may be noted the provision of a novel slide analysis system, a novel slide analysis system which incorporates a multi-function slide transfer device that withdraws individual slides from a slide holding means, positions the slides for spotting and inserts the spotted slides in an incubator, a novel slide analysis system having a universal slide transfer mechanism for moving the slides out of a holding device and into and out of an incubator, as well as positioning the slides for spotting, a slide analysis system having a novel spotting device that accesses a fluid sample at one location and spots a slide at another location, a novel slide analysis system having a novel spotting device with provision for automatic ejection of a pipette tip, a novel slide analysis system having size requirements wherein the components can be made sufficiently compact to permit desk or table-top operation in a physician's office or small laboratory, and a novel method for automatically analyzing slides.

Other objects and features of the invention will be in part apparent and in part pointed out hereinafter.

In accordance with the present invention, the slide analysis system includes an arrangement of components in modular form suitable for operation on a desk top or table top.

The slide analysis system includes a slide holding module for holding a plurality of slide cartridges. Each cartridge in the slide holding module corresponds to a particular person and includes a separate pipette tip and a separate microcup containing serum taken from the person. The respective slide cartridges each accommodate a plurality of slides. Each of the slides in a slide cartridge correspond to a respective test that will be performed on the cartridge serum sample. Each slide cartridge also includes a set of calibration slides used in an incubator.

A predetermined number of slide cartridges are arranged in the slide holding module on a rotatable turntable. One slide cartridge at a time is rotated into a slide withdrawal position, wherein the cartridge aligns with a withdrawal slot formed in the module housing. Slides withdrawn from the slide holding module are transferred to other separate locations for slide spotting and incubation.

The slide analysis system also includes an incubator module spaced from the slide holding module. The incubator module includes a plurality of individual slide retainer stations. Each slide retainer station holds an individual slide from the slide cartridge that is at the slide withdrawal position in the slide holding module. The incubator module includes a single slide insertion slot and a rotatable slide holding tray. The rotatable tray rotates incremental amounts to permit insertion of a new slide in a vacant slide retainer station in sequential order. The incubator also includes an optical head for reflecting light from a chemically treated area of the slide for use in optical analysis of the characteristics of the slide after it has been spotted with serum.

The slide analysis system further includes a slide transfer module or "pick and place" mechanism for withdrawing individual slides from the slide holding module, inserting the slides in the incubator module for a dry fog reading in instances where a dry fog reading is desired, removing the slides from the incubator module after the dry fog reading has been obtained and holding the slides in a spotting position for spotting by a metering module. After the slides have been spotted by the metering module the transfer module or pick and place mechanism reinserts the spotted slide back into the incubator for analysis. After analysis is completed the slide transfer mechanism withdraws the slide from the incubator module and drops it into a discard container.

The transfer module includes a slide engager having jaws that grip against the side edges of a slide when it is necessary to withdraw a slide from the slide holding module or withdraw or insert a slide in the incubator module. The slide engager jaws also grip the slide when it is necessary to transfer the slide from one angular location to another. The slide engager jaws open to release the slide when it is placed in a desired location, and also open to discard a used slide after the analysis is completed.

The slide engager jaws are sized to enter the withdrawal slot in the slide holding module and the incubator slot in the incubator module. The slide engager is rotatable from one orientation to another orientation and the slide engager jaws are transversely movable along the direction of orientation. Thus the slide engager has a compound movement where it can be rotated, and protracted or retracted in its rotated position. The slide engager jaws have a first rotational position wherein the jaws align with the slide withdrawal slot in the slide holding module, a second rotational position wherein the jaws align with the incubator slot in the incubator module, and protracted and retracted positions with respect to each rotational orientation of the slide engager. For example, when the slide engager is retracted from the incubator slot it can hold a slide in a spotting position.

The slide analysis system also includes a metering module for spotting a slide with serum prior to insertion of the slide in the incubator for optical analysis. The metering module includes a metering body that has a first elevated position wherein the metering body is at rest, a first descended position wherein the metering body aspirates serum from a microcup, another descended position wherein the metering body dispenses serum from a pipette tip onto a slide and a further descended position wherein the metering body can eject a pipette tip by means of a built-in pipette tip ejector. The metering body can also self-install a new pipette tip after a used pipette tip has been ejected.

In addition to vertical movement, the metering body has angular movement wherein it is swung into position over a pipette tip in a slide cartridge held in the slide holding module for installation of the pipette tip onto the metering body. The metering body can also be swung from the pipette tip installation position to a sample position wherein the newly installed pipette tip is aligned with a microcup in the slide cartridge that is held in the slide holding module. The metering body lowers the pipette tip into the microcup for aspiration of serum from the microcup and then rises or elevates for further angular rotation into the spotting position. While in the spotting position, the metering body is substantially aligned with the incubator slot in the incubator module.

When the metering body dispenses serum onto the slide it lowers slightly to position the pipette tip in close proximity to the slide that is to be spotted.

When all slides in a particular slide cartridge have been withdrawn for placement in the incubator the pipette tip on the metering body is ejected by a built-in pipette tip ejector. The metering body can then be repositioned over the next sequential slide cartridge in the slide holding module for installation of a new pipette tip and further aspiration of serum from the microcup in the next sequential slide cartridge.

A computerized control system coordinates movement and operation of the various modules of the slide control system.

The invention accordingly comprises the constructions and method hereinafter described, the scope of the invention being indicated in the claims.

DESCRIPTION OF THE DRAWINGS

In the accompanying drawings,

FIG. 6 is an enlarged fragmentary perspective view of system components shown in FIG. 1;

FIG. 7 is an enlarged fragmentary perspective view showing a slide being spotted prior to insertion in the incubator module;

FIGS. 8-10 are fragmentary sectional views showing a spotted slide before and after insertion into the incubator module;

FIG. 14 is an enlarged fragmentary perspective view of the slide transfer device prior to removal of a slide from a slide cartridge in the slide holding module;

FIG. 15 is an enlarged fragmentary sectional view of the slide transfer device engaged with a slide in the slide cartridge;

FIG. 16 is a view similar to FIG. 14 after a slide has been withdrawn from the slide cartridge;

FIG. 17 is a simplified fragmentary plan view of the slide transfer device prior to engagement with a slide in the slide cartridge;

FIG. 18 is a view similar to FIG. 17 after the slide transfer device has engaged a slide in the slide cartridge;

FIG. 19 is a side elevational view of the slide holding module and metering module partly shown in section;

FIG. 20 is an elevational view of the metering module;

FIG. 23 is a simplified fragmentary plan view of the metering module in a pipette installation position;

FIG. 24 is a view similar to FIG. 23 showing the range of movement of the metering module from an aspiration position to a slide spotting position;

FIGS. 25-27 are enlarged fragmentary elevational views showing the metering module prior to and after installation of a pipette tip from a slide cartridge in the slide holding module;

FIGS. 28-30 are enlarged fragmentary sectional views showing the metering module prior to, during and after aspiration of serum from a sample cup in the slide holding module;

FIGS. 31-33 show a slide and cartridge system incorporating another embodiment of the invention;

Corresponding reference characters indicate corresponding parts throughout the several views of the drawings.

DETAILED DESCRIPTION OF THE INVENTION

Figure 1:
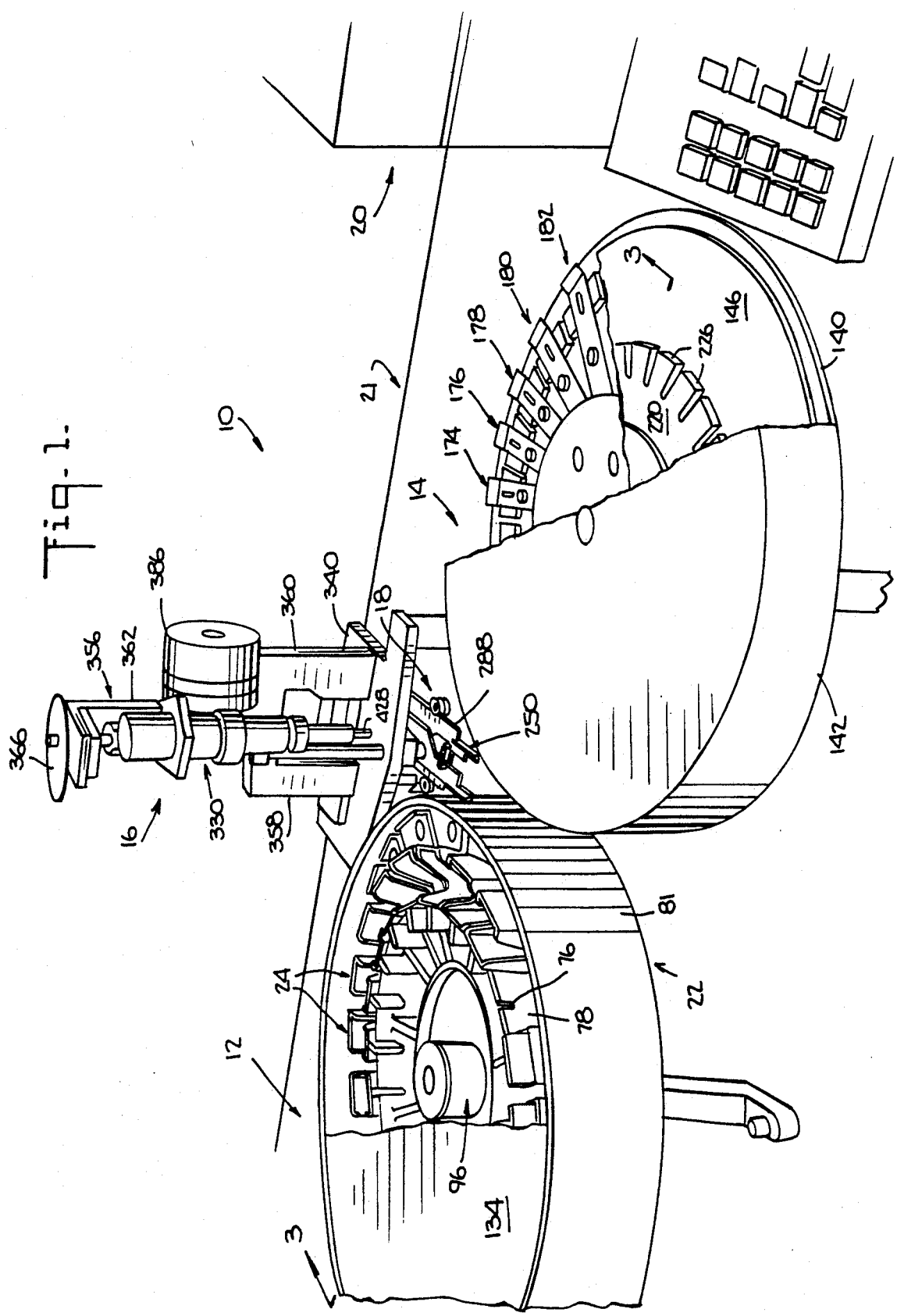
FIG. 1 is a perspective view of a slide analysis system incorporating one embodiment of the invention.

A slide analysis system incorporating one embodiment of the invention is generally indicated by the reference number 10 in FIG. 1.

The system 10 includes a slide holding module 12, an incubator module 14 spaced from the slide holding module 12, and a depositing or metering module 16 for spotting slides with a predetermined amount of serum or fluid, spaced from the slide holding module 12 and the incubator module 14.

The system 10 further includes a slide transfer means 18, also referred to as a pick and place device, arranged below the metering module 16, and a computer control 20 for programming and controlling the operations of the slide analysis system 10. A table top or desk 21 supports the system 10.

The slide holding module 12 includes a generally cylindrical housing 22 that contains a plurality of slide cartridges 24. The slide cartridges 24 are radially spaced around the inside of the housing 22 and detachably seated therein.

Referring to FIGS. 1, 14 and 15, the slide cartridge 24 includes a slide compartment 26 for accommodating a stack of generally rectangular slides 28.

Each slide 28 includes a circular analysis or examination area 29 (FIGS. 7, 9 and 10) with an absorbent receiving surface 31 at a top portion 33 of the slide 28 for spotting with a fluid or serum sample. A translucent barrier strip 35 for preventing evaporation and blocking fluid drainage is provided across the analysis area 29 at a bottom surface 37 of the slide 28. Both the receiving surface 31 and the barrier strip 35 are respectively recessed from the top and bottom surfaces 33 and 37 of the slide 28. For the sake of simplicity, the reference numbers 31 and 35 will also be used to refer to the recessed areas of the receiving surface 31 and the barrier strip 35.

Preferably the wetting surface 31 of each slide 28 in a stack of slides within the compartment 26 has been differently pretreated with selected reagents in a known manner to provide specifically different tests based on the test requirements of a particular individual. Thus each slide cartridge 24 represents a different person. The capacity of the slide holding module can be any selected number of slide cartridges 24 but is preferably twenty slide cartridges.

The slide compartment 26 of a typical slide cartridge 24 is defined by front and rear wall portions 30 and 32, opposite side wall portions 34 and 36 and a base portion 38. U-shaped recesses 40 and 42 are formed in the respective side walls 34 and 36 to facilitate disposition of and access to the slides 28 in the slide compartment 26.

Figure 4:
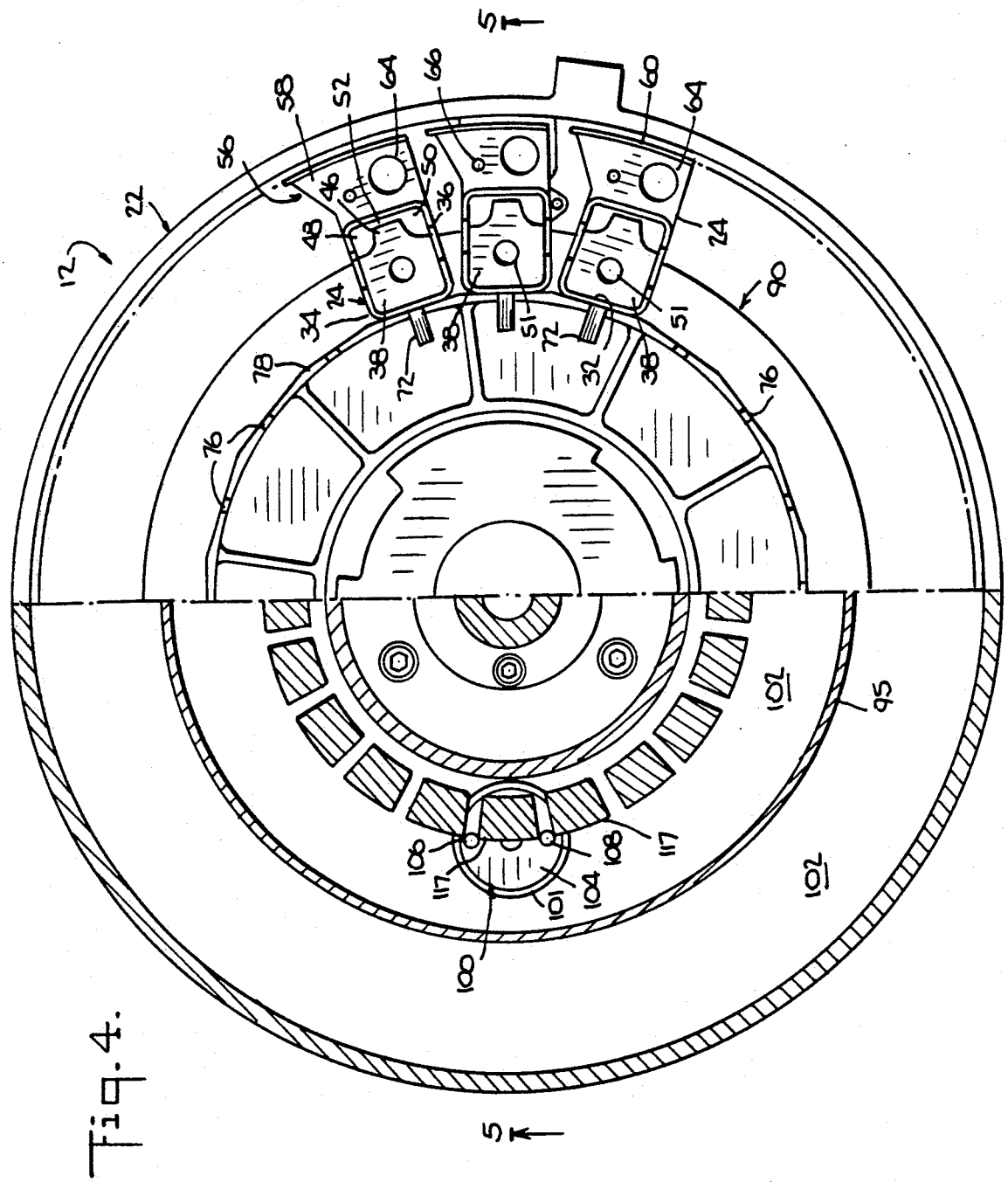
FIG. 4 is a simplified plan view partly shown in section of a slide holding module within the system.

The slide cartridge 24 includes a slide withdrawal slot 44 formed in the front wall 30 and the side walls 34 and 36, at the base portion 38. As most clearly shown in FIG. 4, the base portion 38, in the vicinity of the slide withdrawal slot 44 has a tongue-like formation 46 with side clearance recesses 48 and 50. The base 38 also includes a circular detent boss 51 (FIGS. 4 and 15). The detent boss 51 is formed to engage the recessed area 35 (FIG. 9) at the bottom surface 37 of the lowermost slide 28. Such engagement prevents inadvertent slippage of the lowermost slide 28 from the cartridge 24.

Referring to FIG. 17, the tongue-like formation 46 has a free end 52 foreshortened a predetermined amount from a corresponding edge 54 of a slide 28 supported on the base 38. As most clearly shown in FIG. 15, the height of the slide withdrawal slot 44 from the tongue-like formation 46 is slightly greater than the thickness of a slide 28.

Referring to FIG. 14, a shelf-like appendage 56 is formed on the front wall 30 of the slide cartridge 24 and includes a shelf portion 58 and a data wall 60. The shelf portion 58 is formed with a relatively large opening 64 (FIG. 4) and a relatively small opening 66. The opening 64 detachably accommodates a graduated microcup 68 (FIGS. 14 and 28-30) that contains serum or fluid to be analyzed. The microcup 68 is formed with a cylindrical retainer shell 69 and the shell and cup are collectively referred to as a microcup. The opening 66 detachably accommodates a disposable pipette tip 70 (FIGS. 25-27). The data wall 60 holds, in any suitable known manner, a removable identification slip 62, such as a universal bar code data slip that identifies the source of the test sample as well as any other desirable data.

Figure 5:
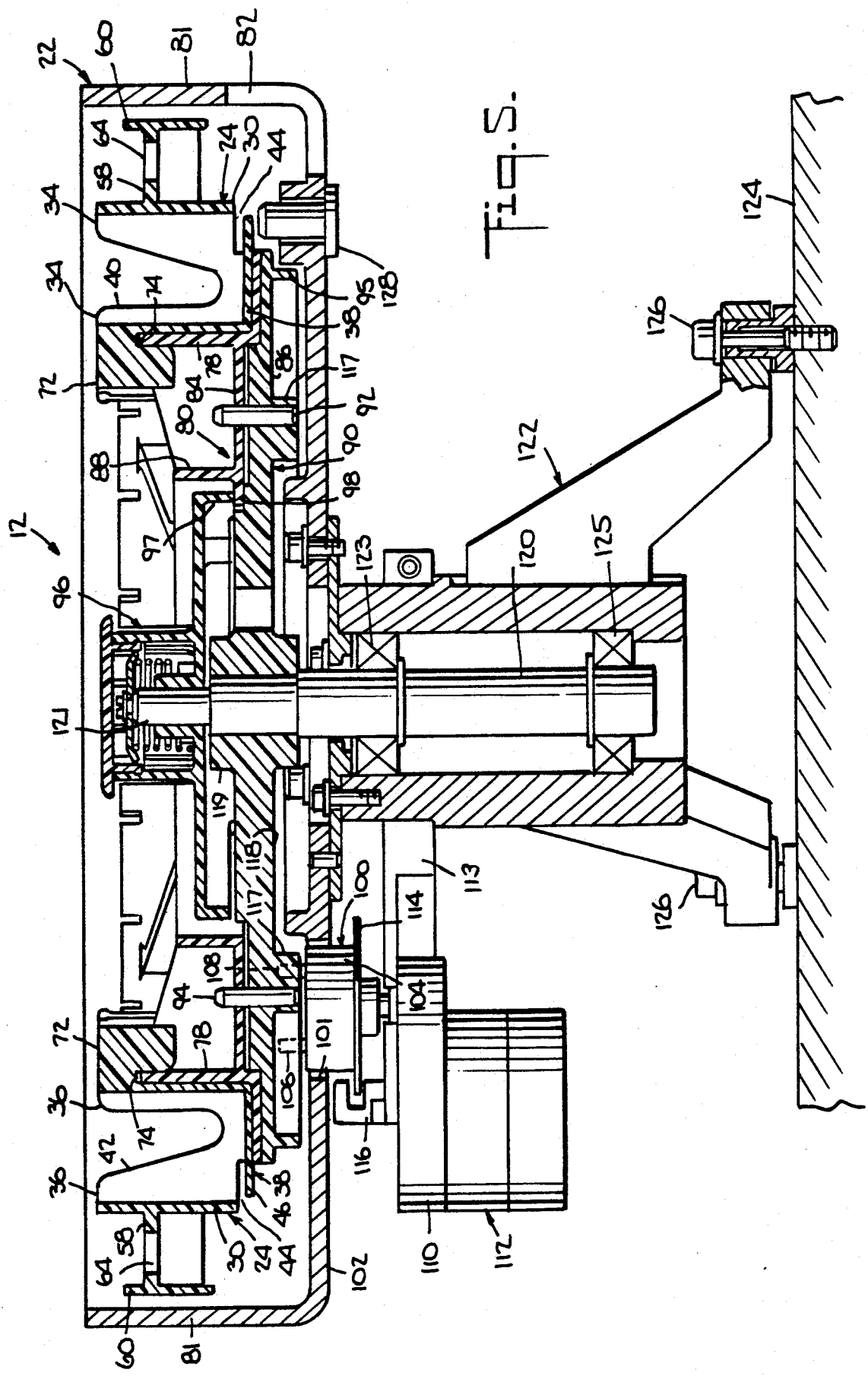
FIG. 5 is a sectional view taken along the line 5—5 of FIG. 4.

Referring to FIGS. 5 and 15, a latch appendage 72 projects from the rear wall 32 of the slide cartridge 24 and is formed with a latch slot 74. The latch slot 74 engages a complementary latch slot 76 (FIG. 1) of an annular support wall 78 of a rotatable cartridge tray 80 provided in the slide holding module 12. A plurality of latch slots 76 are provided in a predetermined spaced relationship on the support wall 78 for accommodating corresponding respective slide cartridges 24.

Occasionally a slide 28 in the cartridge 24 will be inadvertently oriented in an upside-down position, with the receiving surface 31 being downwardly disposed and the barrier strip 35 being upwardly disposed. Thus the receiving surface 31 of the upside-down slide 28 cannot be properly spotted by the metering module 16. Consequently the upside-down slide 28 must be reoriented right-side up in order to yield functional test results, thereby causing interruption of a testing sequence.

Thus a slide cartridge system generally indicated by the reference number 470 in FIG. 31 incorporating a further embodiment of the invention has been developed to avoid the previously described problem of upside-down slide orientation. The system 470 includes a slide 472 generally similar to the slide 28 except that one of the corners 474 of the slide 472 is chamfered.

Referring to FIG. 33, the slide 472 is generally rectangular, with one pair of opposite sides 476 and 478 having a length A that is longer than the other pair of opposite sides 480, 482 having a length B. If desired, the length B can exceed the length A, but should not equal the length A. The slide 472 is otherwise identical to the slide 28 and includes the circular analysis area 29 with a receiving surface 31 at a top portion 484 of the slide. A translucent barrier strip (not shown), identical to the strip 35 is provided at a bottom portion 486 of the slide 472.

Referring to FIGS. 31 and 32, the system 470 further includes a cartridge 490 having a compartment 492 for accommodating the slides 472. The compartment 492 is formed with an internal fillet at the corner 494 to match the chamfered corner 474 of the slide 472. The cartridge 490 is otherwise identical to the cartridge 24. It will be noted that the chamfered corner 474 of the slide 472 and the corner fillet 494 of the cartridge 490 are at predetermined locations to ensure that the cartridge compartment 492 will accommodate the slide 472 in only one orientation wherein the top portion 484 of the slide 472 must face upwardly. Under this arrangement, any slide 472 that is loaded in the cartridge 490 can never be loaded in an upside-down position. All slides 472 loaded into the cartridge 490 are thus properly oriented for spotting of the receiving surface 31. Furthermore, if a bar code (not shown) is provided on the bottom surface 486 of the slide 472, access to such code by a bottom surface bar code reader (not shown) is assured when the slide 472 is always loaded right side up, with the top surface 484 facing upwardly.

Referring to FIGS. 5 and 6, the slide holding module 12 includes an external withdrawal slot 82 provided in an annular wall 81 of the cylindrical housing 22. When the slide withdrawal slot 44 of a slide cartridge 24 aligns with the external withdrawal slot 82 of the cylindrical housing 22, the slide cartridge 24 is characterized to be in a slide withdrawal position. It will be noted that there is only one external withdrawal slot 82 in the annular wall 81 of the cylindrical housing 22. Thus only one slide cartridge 24 at a time, within the slide holding module 12, can be located in the slide withdrawal position.

Referring again to FIG. 5, the rotatable cartridge tray 80 of the slide holding module 12 includes an annular floor portion 84 from which the support wall 78 projects. The floor portion 84 is downwardly stepped at 86 to support the base portion 38 of the slide cartridges 24. The rotatable cartridge tray 80 also includes an inner annular wall 88 that projects from the floor portion 84. The cartridge tray 80 is supported on a turntable 90 which has a peripheral depending flange 95. Pins such as 92 and 94 hold the cartridge tray 80 to the turntable 90.

The slide holding module 12 also includes a detachable hold-down member 96 having an annular flange 97 that bears against an inner peripheral edge portion 98 (FIG. 5) of the cartridge tray floor 84. The hold-down member 96 thus maintains the cartridge tray 80 against the turntable 90.

Figure 3:
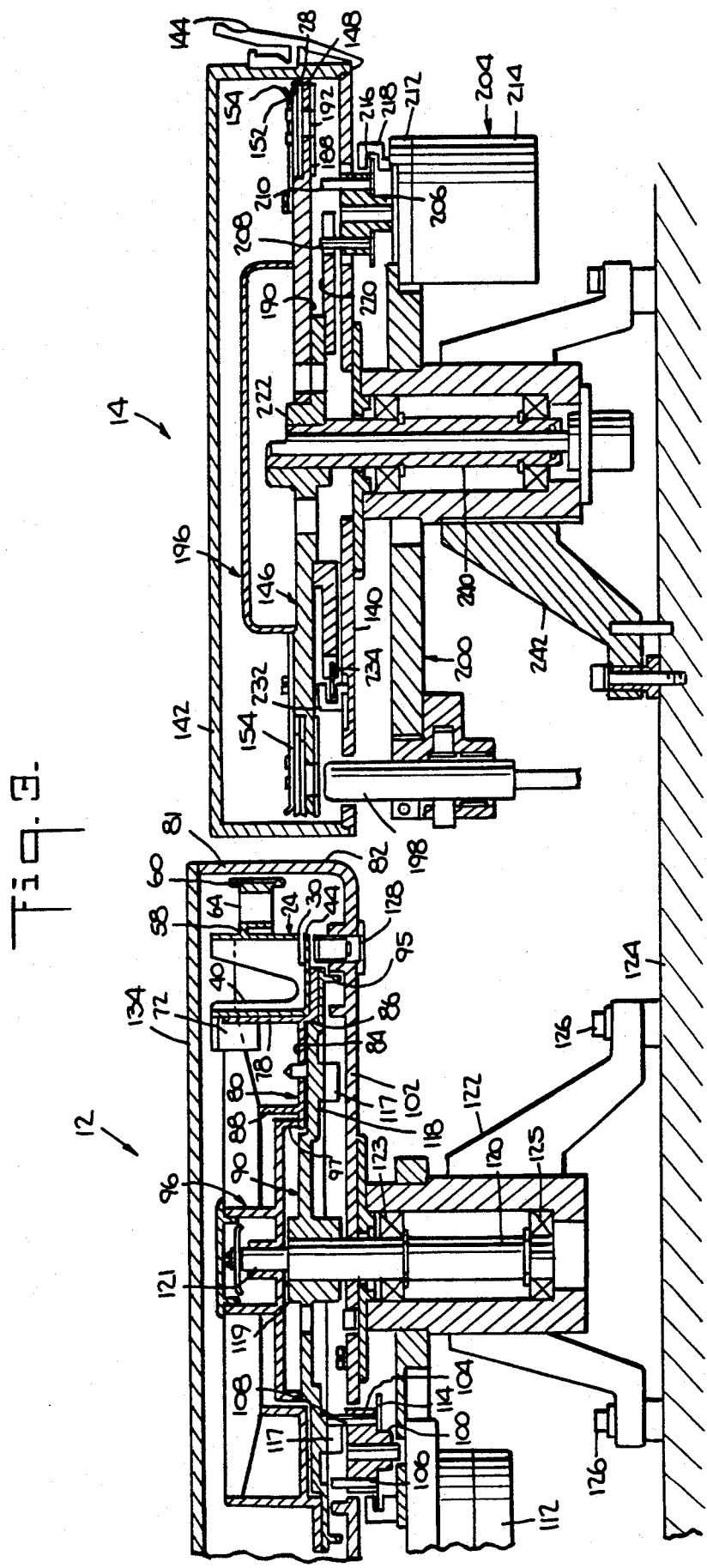
FIG. 3 is a sectional view taken on the line 3—3 of FIG. 1.

Referring to FIGS. 3, 4 and 5, the slide holding module 12 includes a Geneva mechanism 100 that projects through an opening 101 in a base portion 102 to index rotation of the turntable 90 in selected angular increments. The Geneva mechanism 100 includes a rotatable actuator 104 having a pair of spaced actuating pins 106, 108. The actuator 104 is driven through a gear box 110 by a motor 112 joined to a support plate 113. A position flag 114 is provided on the actuator 104 for passage through a homing sensor 116 that senses a predetermined cycle of rotation of the actuator 104.

An underside 118 of the turntable 90 is formed with a plurality of cam lobes 117, spaced in an annular pattern. The cam lobes 117 are generally trapezoidal in cross section (FIG. 4). The actuating pins 106 and 108 are engagable against the cam lobes 117 in sequential order to cause a predetermined incremental rotation of the turntable 90. A hub portion 119 of the turntable 90 is supported for rotation on a shaft 120 that extends through the base portion 102 into a pedestal 122. The pedestal 122 is held in a fixed position on a foundation 124 by fasteners 126. The shaft 120 is journaled for rotation in the pedestal 122 at bearings 123 and 125 in any suitable known manner. The hold-down member 96 is fastened to an extension portion 121 of the shaft 120. The Geneva mechanism 100 is actuated in a known manner in response to a signal sent by an optical sensor 128 (FIG. 15) at the base 102 of the slide housing module 12. The sensor 128 senses the presence of slides 28 in a cartridge 24 that is located at the slide withdrawal position wherein the slide withdrawal slot 46 is aligned with the external withdrawal slot 82 of the cartridge tray 80.

When the sensor 128 fails to sense the presence of a slide 28 in the cartridge 24 due to withdrawal of all slides 28 from the cartridge 24, the sensor 128 signals operation of the Geneva 100. The Geneva 100 thus rotates the turntable 90 a predetermined angular amount to position a new cartridge 24 at the slide withdrawal position in alignment with the external slide withdrawal slot 82.

Although not shown, another optical sensor located next to the sensor 128, senses in a known manner the type of slide 28 that is being withdrawn from the slot 55 of the slide cartridge 24. In addition, a data reader such as a bar code reader 130 (FIG. 6) is affixed to the annular wall 81 above the external withdrawal slot 82. The data reader 130 reads data in a known manner from the identification slip 62 secured to a cartridge 24 when the cartridge 24 is located at the slide withdrawal position.

A cover piece 134 (FIG. 1) is provided on the slide holding module 12 and includes an opening 136 (FIGS. 15 and 25-30) that permits access to the microcup 68 and the pipette tip 70.

The slide holding module 12 thus accommodates, in the preferred embodiment, twenty slide cartridges 24. Each of the slide cartridges 24 corresponds to a particular individual and contains a separate pipette tip 70 and a separate microcup 68 containing the serum sample that corresponds to the individual. Identification of the cartridge 24 with a particular individual is accomplished by means of the data slip 62 provided on the wall portion 60 of the cartridge 24.

The number of slides 28 held by the cartridge 24 determines the number of tests to be performed on the serum sample.

When all the slides in a particular cartridge have been removed for test purposes, the rotatable cartridge tray 80 within the slide holding module 12 is rotated a predetermined amount to enable the next sequential cartridge to be located at the slide withdrawal position wherein the slide removal slot 44 in a cartridge 24 aligns with the external slide withdrawal slot 82 formed in the annular wall of the slide holding module housing 22.

Referring to FIGS. 1, 3, 6 and 7, the incubator module 14, which is of generally cylindrical shape, includes a circular base plate 140 and a cup-shaped cover member 142 detachably secured to the base plate 140 by latch members such as 144 (FIG. 3). A slot 145 (FIG. 2) is formed in the cover member 142 through which slides 28 are inserted or withdrawn from the incubator module 14.

A disk-shaped slide holding tray 146 in the incubator module 14 is fixed to a rotatable shaft 240. The slide holding tray 146 has a stepped down peripheral portion 148 formed with radially spaced bosses o slide bases 150 (FIG. 7). A hold-down piece 152 is biased against each of the slide bases 150 by a resilient clip member 154 fastened to the tray 146 by fasteners 156. The clip member 154 includes an elongated opening 158 (FIG. 8) which receives spaced projections 160 and 162 formed on the hold-down piece 152, to prevent shifting of the hold-down piece 152 with respect to the clip member 154.

The combination of the clip member 154 and the hold-down piece 152 at each slide base 150 constitute respective slide retainers generally indicated by the reference numbers such as 164, 166, 168, 170 and 172 in FIG. 2, 174, 176, 178, 180 and 182 in FIG. 1 (and 168, 170, 172 and 174 in FIG. 7). Although ten slide retainer stations 164–182 are shown in the aforementioned figures, it will be noted that the incubator module 14 has provision for twenty-four slide retainer stations in the preferred embodiment, two of the stations being used to provide calibration readings.

The incubator module 14 includes an annular shaped thermostatically-controlled heater member 188 (FIGS. 7-10) provided at an underside 190 of the peripheral step-down portion 148 of the tray 146. An optical sensor opening 192 is formed at each slide retainer station 164-182 and extends through the heater 188, the stepped down peripheral portion 148 and the respective slide bases 150. The openings 192 align with an analysis area 29 (FIGS. 10 and 16) of each slide 28 held at a respective slide retainer station 164–182.

The incubator module 14 further includes an optical head 198 (FIG. 3) supported in a support plate 200 and extending through a window 202 (FIG. 6) in the base plate 140. The optical head 198 can thus align with the slide analysis areas 29 of a respective slide 28 held in a respective slide retainer station 164-182 when the retainers are successively rotated into alignment with the optical head 198. Such alignment between the optical head 198 and the slide analysis area 29 of a slide 28 is characterized as a slide analysis position.

Figure 34:
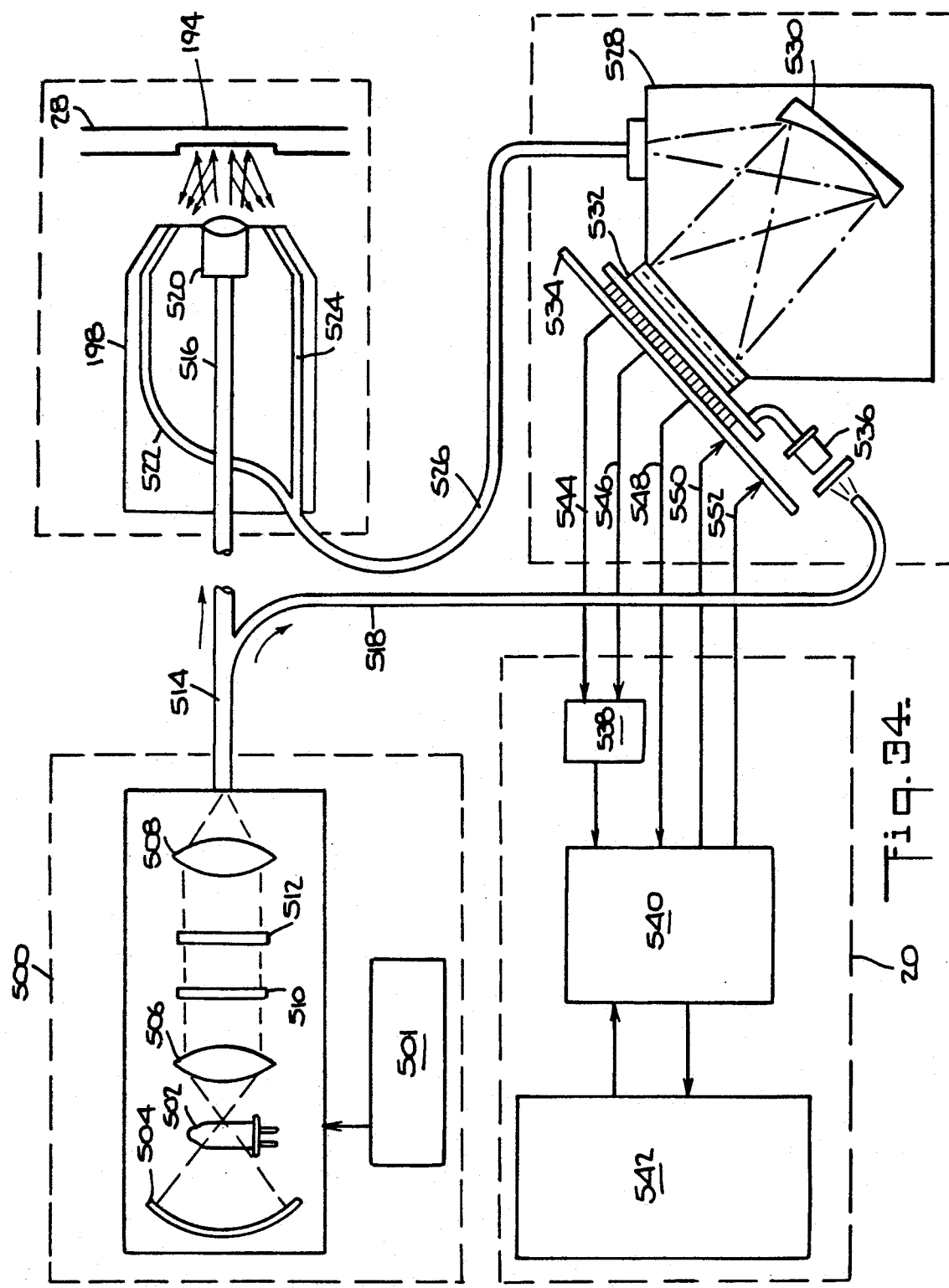
FIG. 34 is a simplified schematic diagram of the optical portion of the slide analysis system.

Referring to FIG. 34, the optical head 198 is fed by an illuminator 500 which includes a power supply 501, a lamp 502, a spherical reflector 504, and a pair of condenser lenses 506, 508. A heat blocking filter 510 and a spectral compensating filter 512 are disposed intermediate the condenser lenses 506 and 508.

Light from the illuminator 500 is transmitted into a fiber optic 514 having a main branch 516 and a reference branch 518. The main fiber optic branch 516 is directed into the optical head 198 terminating in a fiber optic head 520 which directs light onto the slide analysis area 29 of a slide 28 that is in the slide analysis position.

The optical head 198 includes fiber optic branches 522 and 524 which receive light reflected from the slide analysis area 29 back into the optical head 198. The fiber optic branches 522 and 524 merge into a fiber optic cable 526 that communicates with a grating spectrometer 528. The grating spectrometer 528 includes a concave grating 530 that breaks the incoming light from the fiber optic cable 526 into its spectral component parts and projects that spectrum on a self scanning photo diode array or photo detector array 532.

The light coming into the spectrometer 528 is normally nonuniform in energy vs. wavelength. The energies at various wavelengths are not the same and in order to maintain an efficient system it is desirable that all of the energies at the different wavelengths be as similar as possible. The spectral compensating filter 512 helps accomplish such similarity by reducing the energy at some of the very energetic wavelengths. Thus the dynamic range of electronics in the photo detection system of FIG. 31 need not be quite so broad.

The grating array or self scanning photo detector array 532 has every individual element exposed to a different wavelength because of the action of the holographic grating which is incorporated in the grating spectrometer 528. An electronic printed circuit board 534 controls operation of the grating array 532 and has an input with a separate photo detector 536 separate from the grating array 532. The photo detector 536 is for the purpose of establishing a light reference for the system based on light entering along the fiber optic 518 from the illuminator 500. The function of the reference photo detector 536 is to detect any variations in output from the illuminator 500 and compensate for such variations.

The signals to and from the grating spectrometer 528 include a trigger signal 544 and a wavelength data signal 546 fed to an analog to digital converter 538. An end of scan signal 548 is fed to a microcontroller 540 which in turn feeds a start/input signal 550 and a clock signal 552 to the PC board 534. A computer 542 communicates with the microcontroller 540. The computer 542 can be an IBM PC for example and the microcontroller 540 can be an 8031 microcontroller.

It will be noted that the illuminator 500, the grating spectrometer 528, the microcontroller 540, and the computer 542 can be located anywhere within the system 10.

Under this arrangement only one slide retainer station 164-182 at a time within the incubator module 14 can be placed in the slide analysis position, wherein the slide analysis area 29 of a slide 28 aligns, through the opening 192, with the optical head 198.

Referring to FIG. 3, the incubator module 14 further includes an internally disposed cup-shaped cover 196 detachably secured, in any suitable known manner, to the slide holding tray 146 to cover any openings or wires such as 197 (FIG. 7) that extend from the heater 188.

Referring to FIG. 3, a Geneva mechanism 204 is joined to the support plate 200 of the incubator module 14 to index rotation of the slide holding tray 146 by selected angular increments. The Geneva mechanism 204 includes a rotatable actuator 206 having a pair of spaced and projecting actuating pins 208, 210 driven through a gear box 212 by a motor 214. A position flag 216 on the actuator 206 passes through a homing sensor 218 that senses the predetermined incremental rotations of the actuator 206.

Referring to FIGS. 1, 3 and 6, the incubator module 14 also includes a cam plate 220 affixed to a hub 222 at the underside 190 of the slide holding tray 146 such that the hub 222, the cam plate 220 and the slide holding tray 146 rotate in unison with the shaft 240. The cam plate 220 includes spaced peripheral cam-like teeth 226 (FIG. 6) that are engaged in succession by the actuating pins 208, 210 to cause incremental rotation of the slide holding tray 146.

Referring to FIGS. 3 and 6, a position flag 232 projecting from the periphery of the cam plate 220 passes through a homing sensor 234 supported on the base plate 140 to sense a predetermined start-up position of the slide holding tray 146 at the start of a slide analysis cycle.

The incubator module 14 further includes a rotatable shaft 240 that supports the slide holding tray 146 and extends through the base plate 140 from a pedestal 242. The shaft 240 is journaled for rotation in the pedestal 242 in any suitable known manner. The pedestal 242 is held in a fixed position on the foundation 124 by fasteners 244.

Figure 2:
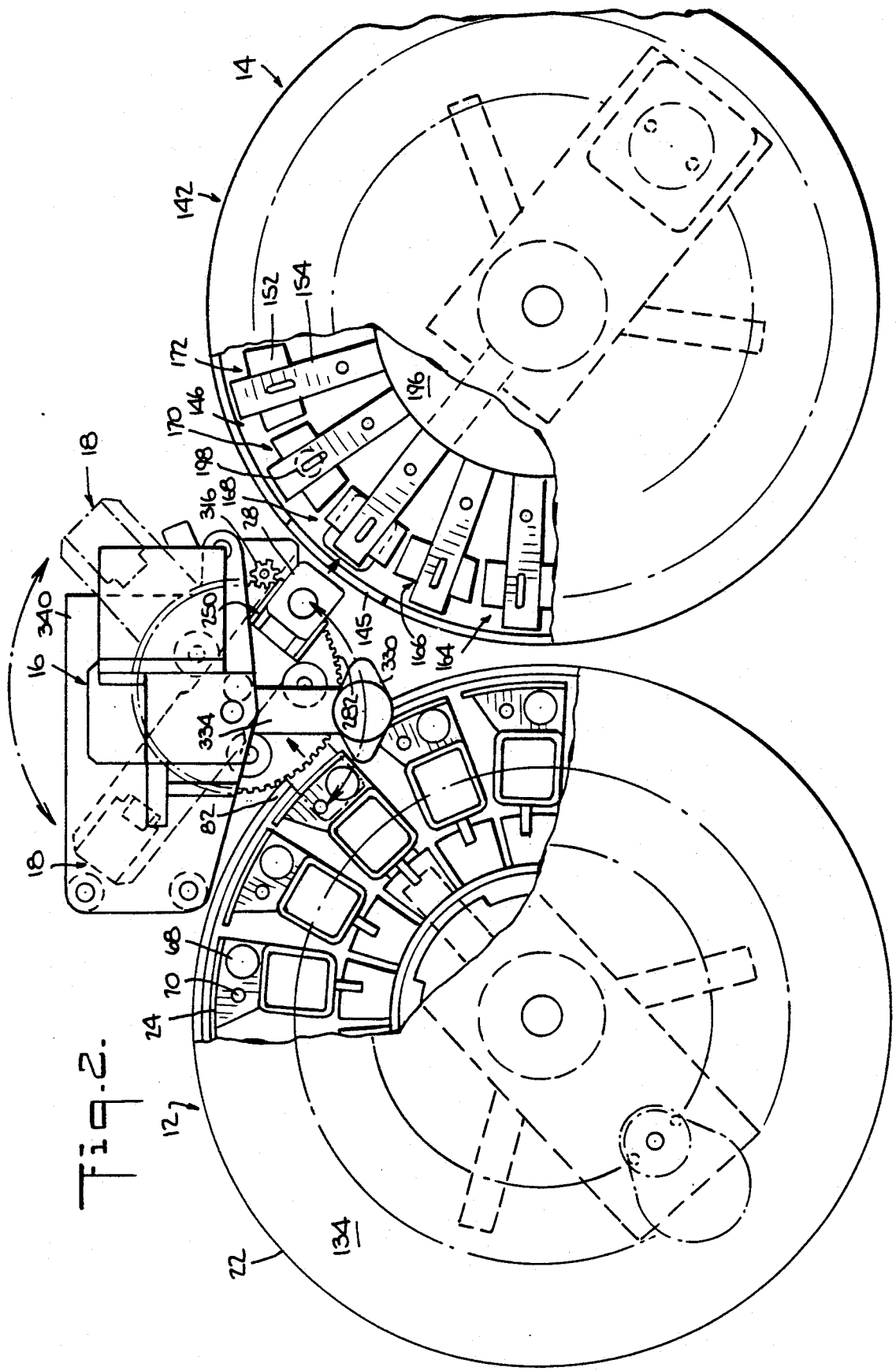
FIG. 2 is a plan view thereof.

Slides 28 are individually inserted into the incubator module 14 through the slot 145 (FIG. 2). For example, when a slide 28 has been spotted with serum and is inserted into the incubator module at slide retainer station 168, the incubator slide holding tray 146 will rotate in a counterclockwise direction, as viewed in FIG. 2, to align the slide retainer station 170 with the slot 145. The slide retainer station 170 is thus ready to receive the next slide 28. As each slide retainer station receives the slide, the slide holding tray automatically rotates a predetermined incremental amount to permit the next sequential slide retainer station to align with the incubator slot for installation of a freshly spotted slide 28. The rotation of the slide holding tray 146 allows each of the spotted slides 28 to pass over the optical head 198 to permit a reflectance reading to be obtained for each slide approximately every 18 seconds. A white, grey and a black reflectance standard (not shown) located in the incubator module 14 are also measured during the rotational cycle of the slide holding tray 146 to provide an optical calibration update for each cartridge of slides.

Referring to FIGS. 11-14, the slide transfer means 18 or pick and place mechanism includes a plier-shaped slide engager 250 for engaging and gripping the opposite sides of a slide 28. The slide engager 250 includes a pair of elongated jaw members 254 and 256 pivoted together at a pivot joint 258. The jaw members 254 and 256 include respective slide support extensions 255 and 257, that are L-shaped in section, for gripping and supporting the side portions of a slide 28. Upper and lower springs 260 and 261 are joined to posts 262 and 264 that project from the jaw members 254 and 256. The springs 260 and 261 normally urge the jaw members 254 and 256 together in a relatively closed position.

Figure 11:
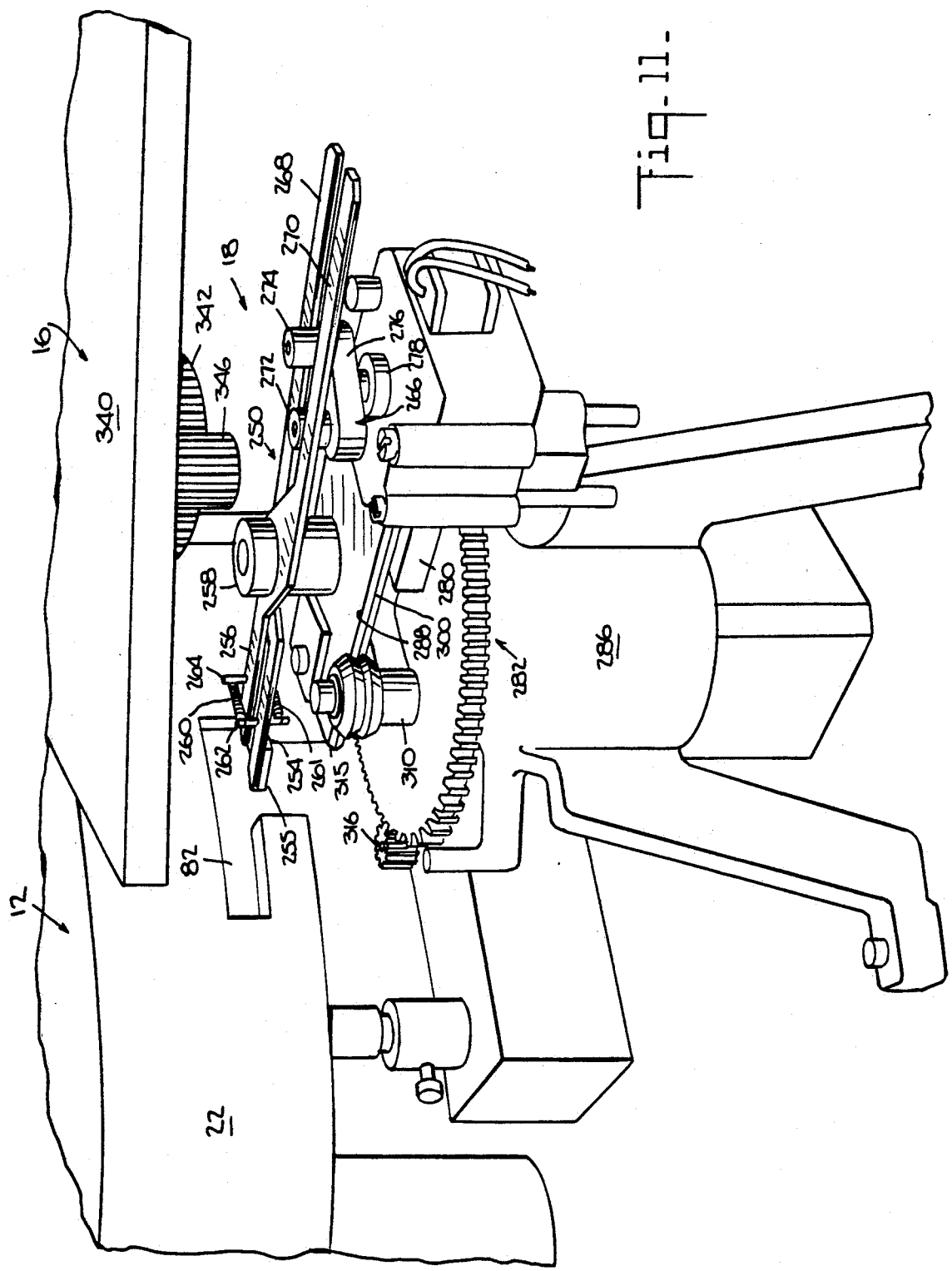
FIG. 11 is an enlarged fragmentary perspective view of the slide transfer mechanism of the slide analysis system.
Figure 12:
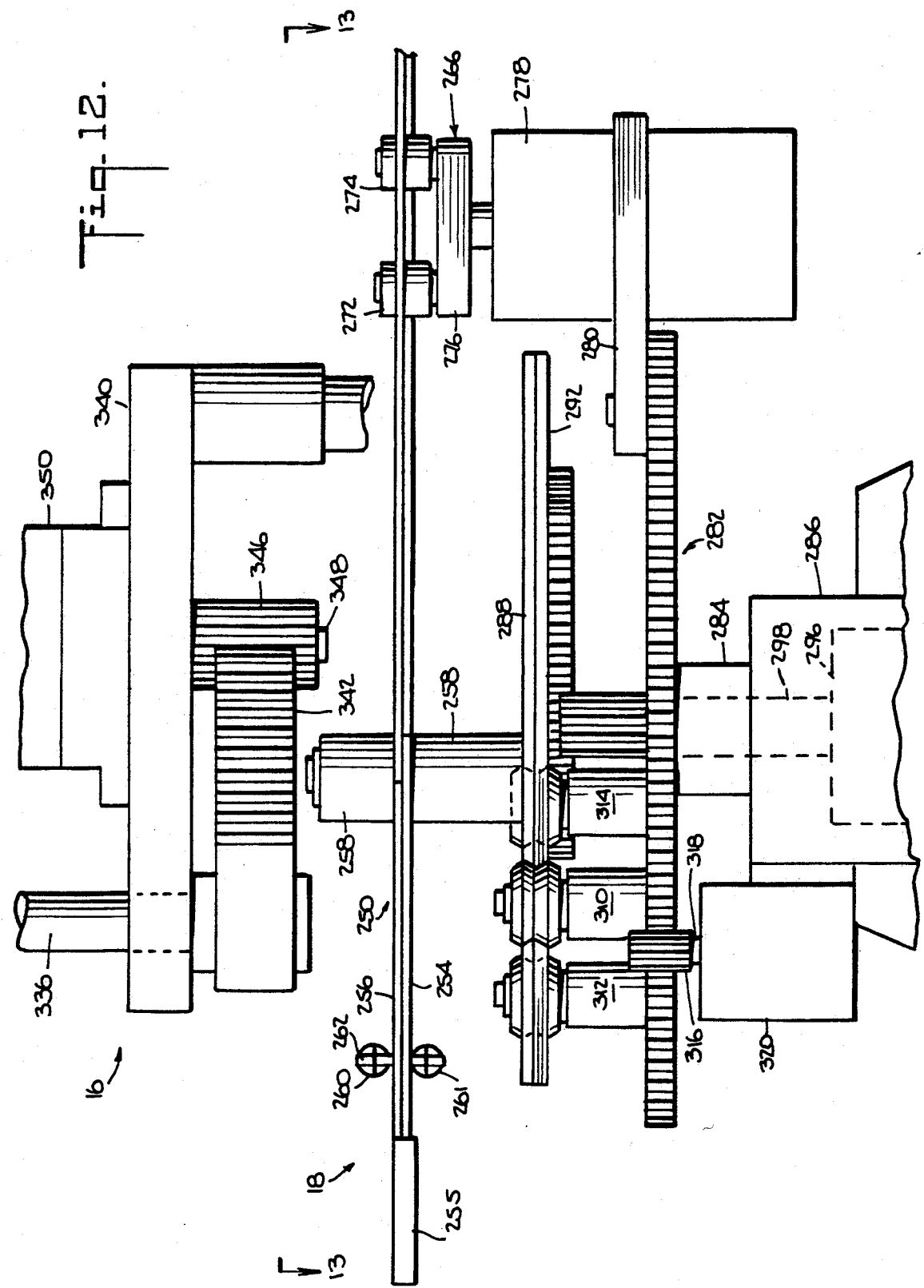
FIG. 12 is an enlarged fragmentary elevational view of structure shown in FIG. 11.
Figure 13:
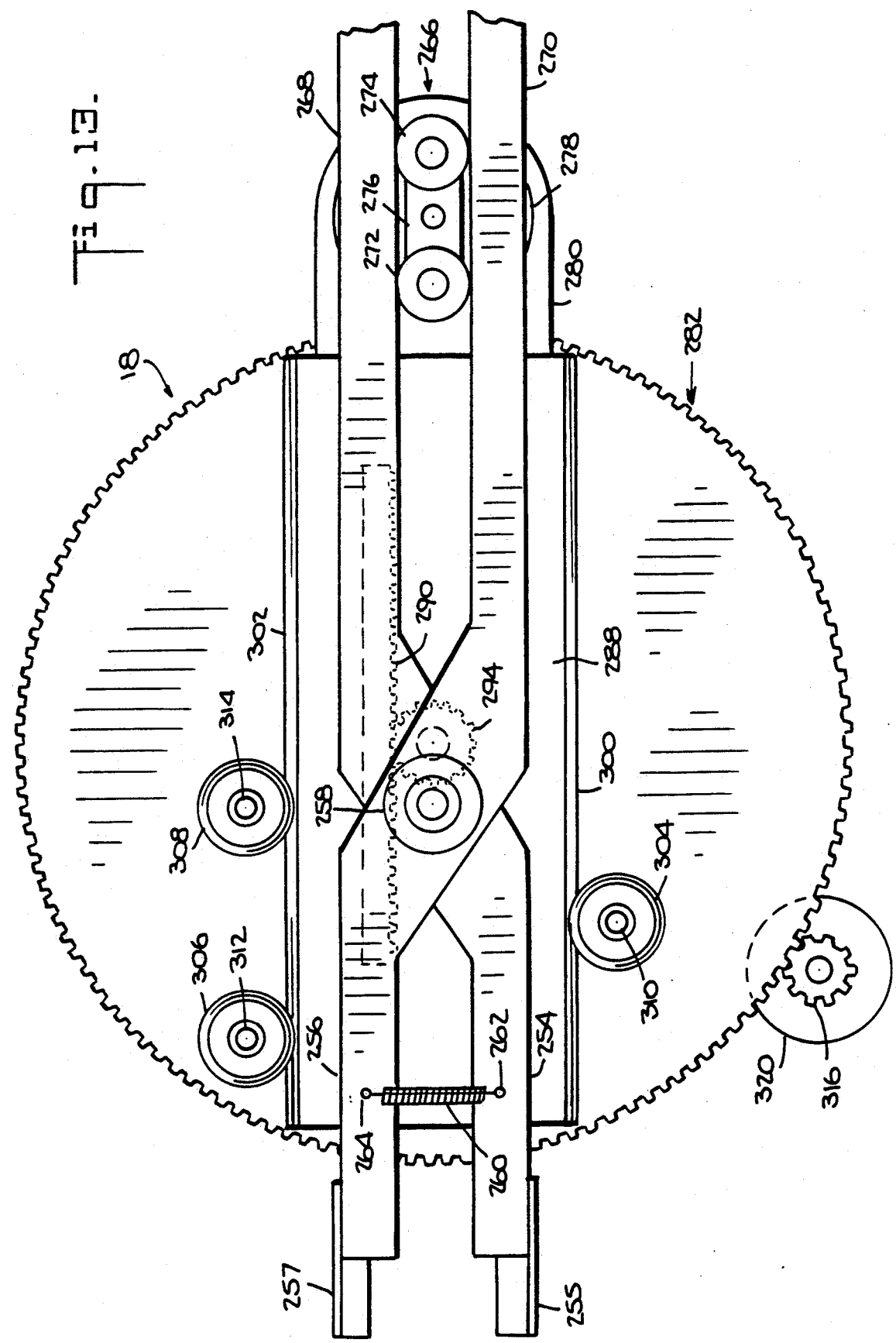
FIG. 13 is a plan view taken along the sight line 13—13 of FIG. 12.

As most clearly shown in FIGS. 11, 12 and 13, a spacer device 266 is provided intermediate extension portions 268 and 270 of the jaw members 254 and 256. The spacer device 266 includes a pair of spaced roller members 272 and 274 projecting from a rotatable actuator 276. A first predetermined rotation of the actuator 276 by a solenoid 278 (FIG. 11) causes the roller members 272 and 274 to overcome the force of the springs 260 and 261 to separate the jaw members 254 and 256 from the relatively closed position of FIG. 13 to the relatively open position of FIG. 14. A second predetermined rotation of the actuator 276 by the solenoid 278 enables the springs 260 and 261 to urge the jaw members 254 and 256 into their relatively closed position.

As most clearly shown in FIG. 12, the solenoid 278 is joined to a main gear 282 by a support plate 280 that is fixed to the main gear 282 by a fastener 283. The main gear 282 is supported for rotation by a shaft 284 mounted in a pedestal 286.

Referring to FIG. 12, the pivot joint 258 for the jaw members 254 and 256 is supported on an elongated movable plate 288. A rack member 290 is provided at the underside 292 of the plate 288 for engagement with a pinion 294. A motor 296 supported in the pedestal 286 includes a shaft 298 for driving the pinion 294.

Referring to FIGS. 12 and 13, opposite elongated edge portions 300 and 302 of the plate 288 are supported by grooved rollers 304, 306 and 308 that are respectively rotatably mounted on posts 310, 312 and 314 affixed to the main gear 282. The edge portion 300 of the elongated plate 288, which engages the roller 304, and the opposite edge portion 302 which engages the rollers 306 and 308, are crested as noted at 315 (FIGS. 14 and 16) for complementary engagement with the grooved rollers 304-308.

Referring again to FIGS. 12 and 13, a pinion gear 316 is engagable with the main gear 282 for effecting rotation of the main gear 282. The pinion gear 316 is fixed to the shaft 318 of a drive motor 320 that is supported on the pedestal 286.

Under this arrangement, rotation of the pinion gear 316 a predetermined amount causes a predetermined rotation of the main gear 282 to orient the jaw members 254 and 256 in a selected direction. Rotation of the pinion gear 294 by the motor 296 causes transverse movement of the rack 290 and the movable plate 288 to transversely move the jaw members 254 and 256 a predetermined amount in their direction of orientation. The actuator 276, when rotated approximately. 90° by the motor 278, causes the roller members 272 and 274 to diverge the jaw members 254 and 256 a predetermined amount to accommodate a slide 28. Further rotation of the actuator 276 an additional approximate 90° enables the jaw members 254 and 256 to converge under the influence of the spring member 260 to grip the side edges of the slide 28.

The slide transfer means 18 is thus capable of orienting the plier-shaped engager means 250 in alignment with the external withdrawal slot 82 of the slide holding module 12 in the manner shown in FIG. 11. Such alignment is accomplished by rotation of the main gear 282 a predetermined amount by the pinion 316. Since the main gear supports the support plate 280 via the support posts 310, 312 and 314, the rotation of the main gear 282 causes corresponding rotation of the support plate 288, which has a fixed angular orientation with respect to the main gear 282.

The slide engager 250 also has a fixed angular orientation with respect to the support plate 288. Thus rotation of the main gear 282 causes corresponding rotation of the plier-shaped slide engager 250.

Once the slide engager 250 is aligned with the external withdrawal slot 82 of the slide holding module, the pinion 294 (FIGS. 12 and 13), when rotated in a counterclockwise direction as viewed in FIG. 13, will cause the rack 290 to transversely move the support plate 288 and the plier-shaped slide engager 250 transversely in the direction of alignment with the external withdrawal slot 82.

As the plier-shaped jaw engager 250 moves into the external withdrawal slot 82 in the manner shown in FIG. 15, the jaw members 254 and 256 diverge a predetermined amount in response to movement of the spacer device 266 from the position of FIG. 13 to a rotational position approximately 90° offset from the position of FIG. 13.

The support plate 288 is moved a predetermined amount by the pinion 294 and rack 290 to position the jaw members 254 and 256 alongside opposite side portions of a slide 28 held in a cartridge 24 in the manner shown in FIG. 17. The spacer device 266 then rotates a predetermined amount of approximately 90° to permit the spring members 260 and 261 on the jaw members 254 and 256 to urge the jaw members into a relatively closed position of FIG. 18 wherein the support extensions 255 and 257 engage and grip the opposite side portions of a slide 28. The slide engager 250 having gripped a slide 28 in the manner shown in FIG. 18 is retracted from the external withdrawal slot 82 by reverse transverse movement of the support plate 288 in response to clockwise rotation of the pinion 294 as viewed in FIG. 13. The slide engager thus carries the slide 28 in the manner shown in FIG. 16 to the incubator module 14 in the manner shown in FIG. 2 wherein the slide transfer means 18 is rotated in a counterclockwise direction as viewed in FIG. 2 to accomplish movement from the slide holding module 12 to the incubator module 14.

Movement of the slide engager 250 from the slide holding module 12 to the incubator module 16 is accomplished by clockwise rotation of the pinion 316 a predetermined amount as viewed in FIG. 13 to cause counterclockwise rotation of the main gear 282 a predetermined amount sufficient to align the slide engager 250 with the slot 145 (FIG. 2) in the incubator 14.

Once the slide engager 250 is aligned with the slot 145 in the incubator 14 the pinion 294 (FIG. 13) rotates counterclockwise a predetermined amount to cause movement of the slide engager 250 and the slide 28 into the incubator module 14 through the slot 145 to position the slide 28 at a slide retainer station 168 (FIGS. 2 and 7). After the slide 28 is sandwiched between the holddown piece 152 and the slide base 150 at the slide retainer station 168 in the manner shown in FIG. 9, the jaw members 254 and 256 of the slide engager means are diverged once again by the spacer device 266. Thus the slide engager 250 is retracted from the incubator module 14 without the slide 28.

In instances where it is necessary to remove a slide 28 from the incubator module 14, the slide engager 250 is protracted through the slot 145 in the incubator module 14 with diverged jaw members 254 and 256 until such jaw members are located alongside the opposite edge portions of the slide 28 in a manner similar to that shown in FIG. 17. The jaw members 254 and 256 and the respective extension pieces 255 and 257 are caused to converge against the side edges of the slide member 28 in a manner similar to that shown in FIG. 18. Such convergence of the jaw members 254 and 256 is attributable to rotation of the spacer member 266 a predetermined amount to enable the spring members 260 and 261 on the slide engager to converge the jaw members 254 and 256 against the edge portions of the slide 28. The slide 28 can then be removed from the incubator and transferred by the slide transfer means 18 to any selected position.

The slide transfer device 18 thus has linear motion in protracting the slide engager means into the slide holding module 12 and the incubator module 14 as well as retracting the slide engager 250 from the respective slide holding and incubator modules 12 and 14. The slide transfer device 18 also has two angular positions, the first of which allows access to the slide holding module 12, the second of which allows access to the incubator module 14. It will also be noted that the slide 28 is spotted by the metering module 16 when it is aligned with the slot 145 in the incubator module in the manner which will be subsequently described.

Referring to FIG. 19, the depositing or metering module 16 for spotting slides 28 includes a metering body 330 having a frame extension 334 that is axially slidable on a shaft 336.

Referring to FIG. 20, the shaft 336 has an end portion 338 rotatably mounted in and extending below a base plate 340. Transfer means for moving the metering head 330 toward and away from the slide holding module 12 and to other positions such as a metering location for depositing serum onto a slide 28 include a sector gear 342. The sector gear 342 is fixed to an end portion 338 of the shaft 336 below an underside 344 of the base plate 340. The sector gear 342 is driven by a pinion gear 346 fixed to a shaft 348 of a motor 350 mounted on the base plate 340.

An opposite end portion 352 of the shaft 336 is rotatably supported in an arm 354 of a support frame 356 having spaced legs 358 and 360 (FIG. 1) mounted on the base plate 340. A trunk portion 362 of the support frame 356 extends from the legs 358 and 360, and includes an end portion 364 that joins the arm 354 (FIG. 23). Under this arrangement, rotation of the pinion 346 causes rotation of the sector gear 342, which rotates the shaft 336 to swing the metering body 330 from one selectable position to another selectable position such as, for example, from the position of FIG. 23 to the position of FIG. 24.

A flag member 366 (FIG. 20) is provided at the shaft end portion 352, being affixed to a holding collar 368 that is fastened to the end portion 352. A sensor device 370 is arranged on the arm 354 to sense angular movement of the flag member 366 based on rotational movement of the shaft 336.

Referring again to FIG. 20, a yoke member 372 having upper and lower arms 374 and 376 is slidably mounted to the shaft 336. The yoke member 372 further includes a back portion 378 that joins the arms 374 and 376. The back portion 378 is formed with or otherwise supports a rack 380. The rack 380 engages a pinion 382 driven by a bi-directional motor 386 supported on the trunk portion 362 of the support frame 356. One or more pins 388 extending from the trunk portion 362 are arranged to slightly touch the back portion 378 to prevent rotation of the frame 334 with respect to the shaft 336, without interfering with slidable movement of the frame 334 with respect to the shaft 336.

Referring to FIG. 20, the frame 334 is biased against the arm 376 of the yoke member 372 by a dampening spring 390. The dampening spring 390 is provided on the shaft 336 between the arm 374 and the frame 334 thus spacing the frame 334 from the arm 374.

When the motor 386 causes the pinion 382 to rotate in a counterclockwise direction as viewed in FIG. 20, the rack 380 moves in a downward direction with the yoke member 372, thus urging downward movement of the frame 334 and the metering body 330. The dampening spring 390 assures a smooth transfer of movement from the yoke member 372 to the frame 334.

Downward movement of the metering body 330 is needed during installation of a pipette tip 70 to the metering body as shown in FIGS. 25 and 26, and for the purpose of aspiration of fluid into the pipette tip 70 from the microcup 68 as shown in FIGS. 28 and 29. Downward movement of the metering body is also needed for the purpose of spotting a slide 28 as shown in FIG. 21.

Figure 21:
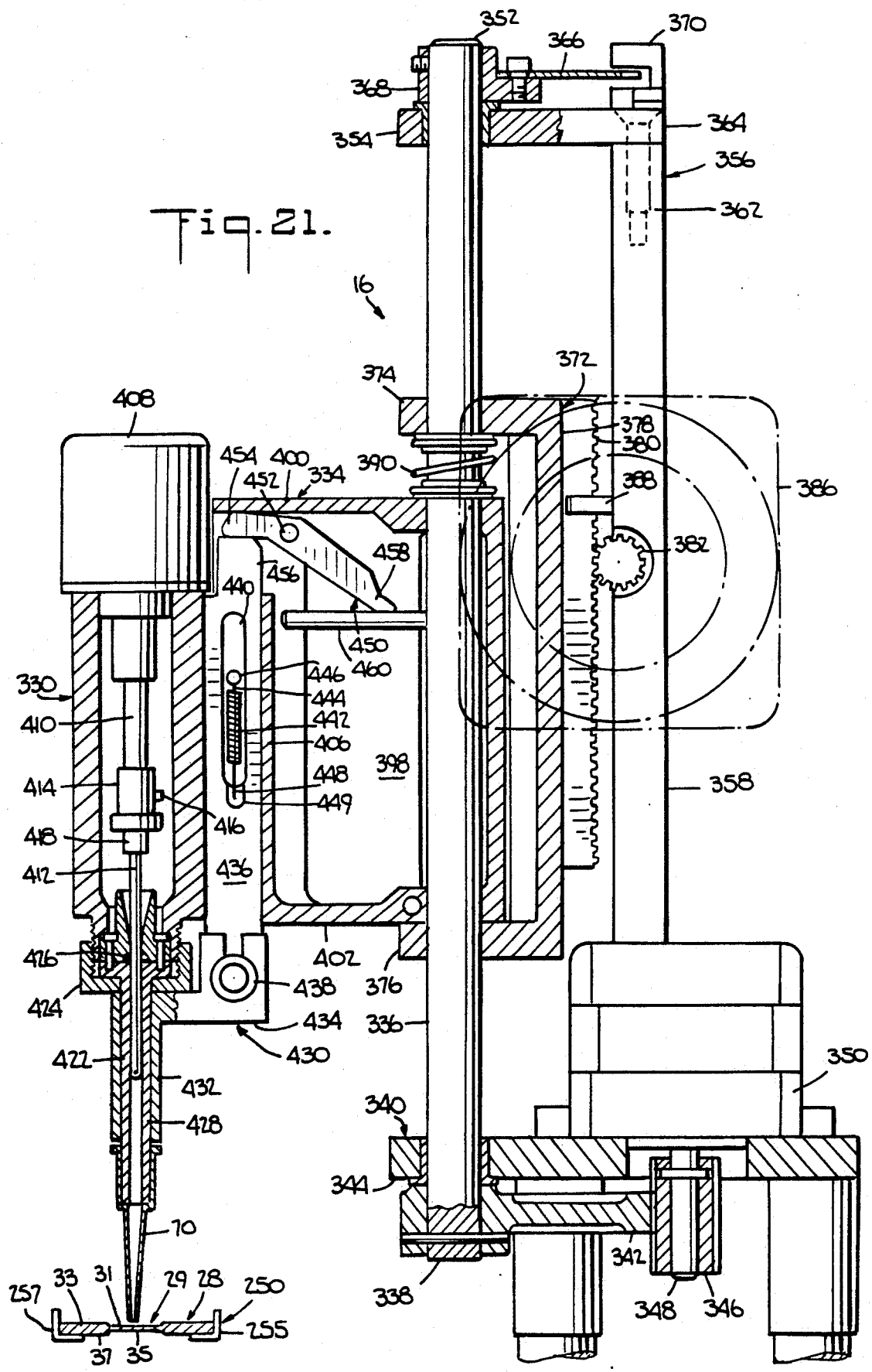
FIG. 21 is an elevational view, similar to FIG. 20, of the metering module during slide spotting.
Figure 22:
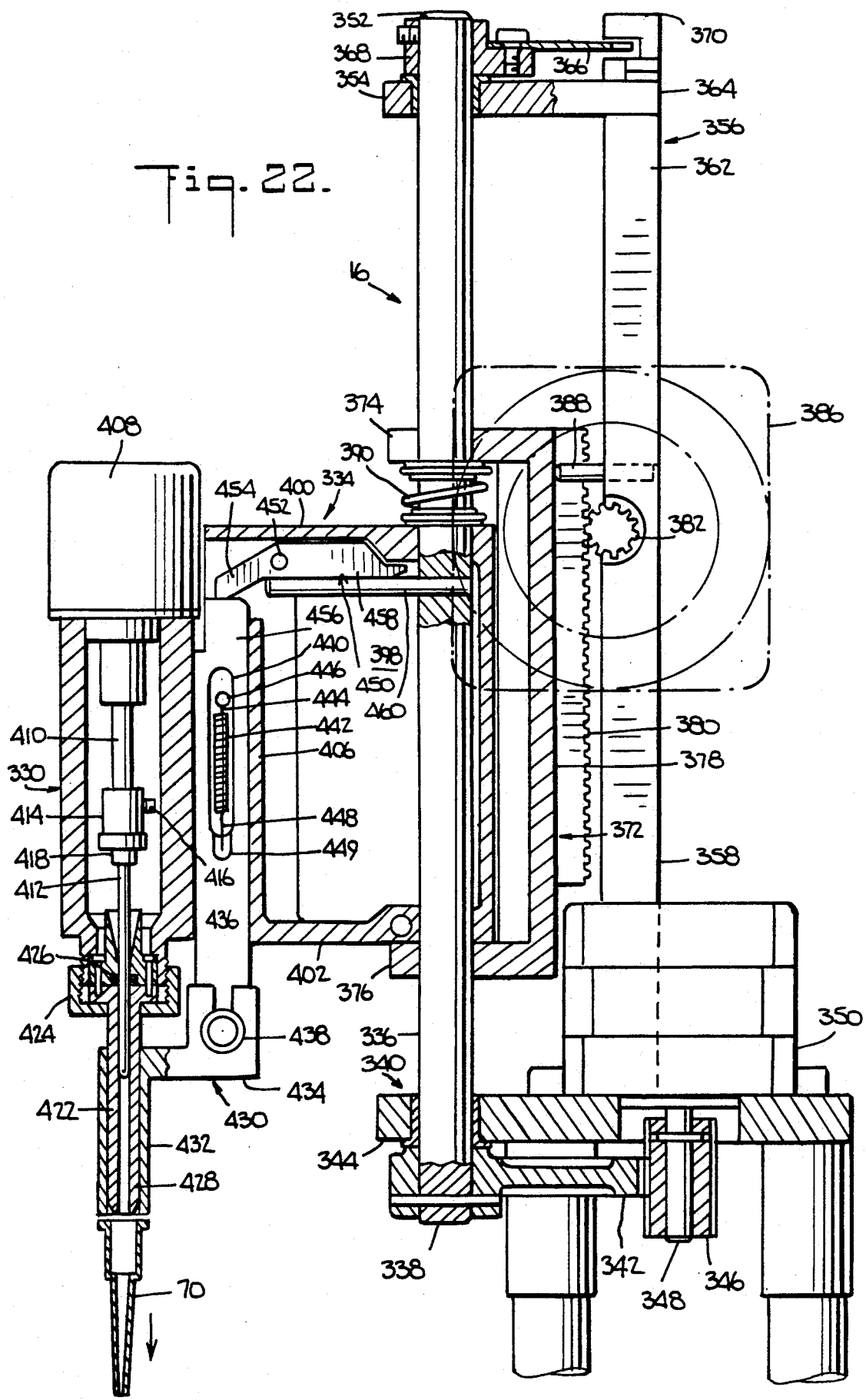
FIG. 22 is an elevational view similar to FIG. 21 of the metering module during ejection of a pipette tip.

Upward movement of the metering body 330 is accomplished by rotation of the pinion 382 in a clockwise direction as viewed in FIGS. 21 and 22. Clockwise movement of the pinion 382 causes the rack and yoke 372 to move in an upward direction relative to the shaft 336, thereby urging the frame 334 and the metering body 330 to move in an upward direction. Upward movement of the metering body 330 is needed to elevate the metering body 330 from the slide holding module 12 after a pipette tip 70 has been installed on the metering body 330 as shown in FIGS. 26 and 27. Upward movement of the metering body 330 is also needed after the pipette tip 70 has aspriated fluid from the microcup 68 as shown in FIGS. 29 and 30. The upper limit of movement for the metering body 330 is the rest position shown in FIG. 20. The metering body 330 returns to the rest position after it has moved downwardly for the purpose of installation of a pipette tip 70, aspiration of serum from a microcup 68, spotting of a slide 28 and automatic ejection of a pipette tip 70.

The metering body 330 is thus capable of moving upwardly and downwardly when aligned with a slide cartridge 24 in the slide holding module 12 as shown in FIG. 23. The metering body 330 is further capable of moving upwardly and downwardly when aligned with a slide 28 held in a spotting position by the slide transfer means 18 as shown in FIG. 24. Thus the metering body 330 can be swung from an aspiration position, indicated by the centerline 391 in FIG. 24, to a spotting position, indicated by the centerline 393 in FIG. 24. In each of the aspiration and spotting positions the metering body 330 can be raised or lowered predetermined amounts.

Referring to FIGS. 19 and 20, the metering body 330 and the frame 334 are preferably formed in two mating half portions fastened together in any suitable known manner. Thus the metering body 330 comprises a front cylindrical shell portion 392 (FIG. 19) and the frame 334 comprises a front plate portion 394 extending integrally from the front shell portion 392. The metering body 330 also includes a rear cylindrical shell portion 396 (FIG. 20) and the frame 334 includes a rear plate 398 extending integrally from the rear shell portion 396.

Referring to FIG. 20, the front and rear plate portions 394 and 398 are spaced by upper and lower ribs or walls 400, 402 and side ribs or walls 404, 406.

The metering body 330 includes a pump 408 having a shaft 410 that is actuatable to protract or retract predetermined amounts in the axial direction of the shaft 410. A plunger 412 is connected to the shaft 410 via a connecting sleeve 414 that locks to the shaft 410 by a lock screw 416. The plunger 412 is joined to a swivel piece 418 that is received in a cap member 420. The cap member 420 is threaded onto the sleeve 414.

The plunger 412 is receivable in a pumping tube 422 that is joined to the metering body 330 by the threaded cap 420. A slight swivel capability of the swivel piece 418 relative to the cap 424 enables the plunger 412 to compensate for any axial misalignment between the plunger 412 and the pumping tube 422.

The pumping tube 422 is provided with an O-ring 426 to seal around the plunger 412 during axial movement of the plunger 412 by the pump shaft 410. An end portion 428 of the pumping tube 422 holds the pipette tip 70 in press-fitting relationship.

Referring again to FIG. 20, a pipette tip ejector 430 for the pipette 70 includes a cylindrical sleeve portion 432 slidably disposed on the pumping tube 422 between the pipette tip 70 and the cap 424. The pipette ejector 430 further includes a connection arm 434 detachably secured to a slide member 436 by a fastener 438. The slide member 436 is slidably disposed in the frame 334 between the metering body 330 and the side rib 406 on the rear plate 398. The slide member 436 includes an elongated slot 440 which accommodates a return spring 442. One end portion 444 of the return spring 442 is affixed to a post 446 supported in the rear plate 398. An opposite end portion 448 of the return spring 442 is affixed to the slide member 436 in a groove 449. Under normal conditions the return spring 442 maintains the slide member 436 in the position shown in FIG. 20.

The pipette tip ejector 430 further includes an actuator arm 450 pivoted at 452 such that an end portion 454 of the actuator arm 450 is confined between an end portion 456 of the slide member 436 and the upper rib 400 of the frame 334. An opposite end portion 458 of the actuator arm 446 extends toward the shaft 336. A pin 460 affixed to the shaft 336 and extending toward the metering head 330 is arranged to interfere with the end portion 458 in the manner shown in FIGS. 21 and 22 when the pinion 382 drives the rack 380 a predetermined amount toward the base plate 340.

The pipette tip ejector 430 comes into operation after all of the slides 28 in an individual cassette 24 have been removed from the cassette 24. The pipette tip 70 which is associated with the empty cassette 24 must now be removed and discarded to permit installation of a fresh new pipette tip 70 that is associated with a next sequential slide cassette 24 in the slide holding module 12.

The pipette tip 70 is ejected from the metering body 330 when the pinion 382 rotates in a counterclockwise direction as viewed in FIG. 22 to cause the rack 380 and the yoke 372 to move downwardly on the shaft 336 toward the base plate 340. Downward movement of the yoke 372 causes corresponding downward movement of the frame 334 to a downward limit position as shown in FIG. 22 wherein the pin 460 interferes with the actuator arm 450 in the manner shown in FIGS. 21 and 22.

Pivotal movement of the actuator arm 450 in a counterclockwise direction about the pivot 452 as shown in FIGS. 21 and 22, causes the end portion 454 of the actuator arm to drive the slide member 436 downwardly relative to the frame 334 and the metering body 330. Downward movement of the slide member 436 results in corresponding downward movement of the ejector sleeve 432 that surrounds the pumping tube end portion 428. The ejector sleeve 432 thus pushes the pipette tip 70 from the pumping tube end portion 428 enabling the pipette tip 70 to drop away from the pumping tube end portion 428 in the manner shown in FIG. 22. It will be noted from a comparison of FIGS. 21 and 22 that downward movement of the metering body 330 to spot a slide 28 as shown in FIG. 21 does not cause movement of the ejector 430. Movement of the ejector 430 is initiated after the metering body 330 and the frame 334 are caused to move downwardly beyond the spotting position of FIG. 21 as shown in FIG. 22.

Movements of the metering module 16 are coordinated with movements of the slide transfer device 18 as well as movements of the turntable 90 within the slide holding module 14 and the slide holding tray 146 within the incubator module 14.

At the startup of operation of the slide analysis system 10, a cartridge 24 is aligned with the external slide withdrawal slot 82 in the slide holding module 12. The metering module 16 self installs a pipette tip 70 from the slide cartridge 24 that is in the slide withdrawal position. It will be noted that all slide cartridges 24 disposed in the slide holding module 12 are equipped with corresponding pipette tips 70 and microcups 68 that are used only for the slides within the respective slide cartridge 24.

The metering module 16 self installs the pipette tip 70 when the pinion 346 in rotated in a counterclockwise direction as viewed in FIG. 23 to cause clockwise rotation of the sector gear 342 thereby swinging the metering body 330 into alignment with the pipette tip 70 located in the cartridge 24 that is in the slide withdrawal position. The metering body 330 can thus be lowered in the manner shown in FIGS. 25-27 to cause engagement between the end portion 428 of the pumping tube 422 with the pipette tip 70. It will be noted that the free end 428 of the pumping tube 422 as shown in FIG. 25 is tapered to facilitate installation and removal of the pipette tip 70.

After the pipette tip 70 has been installed on the metering body 330 and before a first slide is spotted, the metering body is aligned by predetermined rotation of the sector gear 342 by the pinion 346 with the microcup 68. The metering head 330 is then lowered by counterclockwise engagement between the pinion 382 and the rack 380 as viewed in FIG. 20 to permit the sequence of operations represented by FIGS. 28 and 29.

With the metering body 330 in the position of FIG. 29 the pump 408 causes retraction of the shaft 410 a predetermined amount. The pump plunger 412 thus retracts a predetermined amount in the pumping tube 422 to aspirate a predetermined volume of fluid from the microcup 68 into the pipette tip 70.

As most clearly shown in FIG. 30 the amount of fluid aspirated by the pump 408 into the pipette tip 70 never exceeds a level which would cause contact between the aspirated fluid and the end portion 428 and the pumping tube 422. Thus the possibility of cross contamination between serum samples from different microcups 68 is avoided. Furthermore the amount of dosage of serum aspirated into the pipette tip 70 is sufficient to spot one slide 28. Thus after the aspiration operation has taken place the metering body 330 elevates from the position of FIG. 29 to the position of FIG. 30 to permit movement of the metering body 330 from the aspiration position represented by the reference number 391 in FIG. 24 to the spotting position represented by the reference number 393 in FIG. 24.

With the metering body 330 located in the spotting position 393 of FIG. 24, the pump 408 causes the shaft 410 to protract a predetermined amount. Protraction of the shaft 410 causes the pump plunger 412 to protract a predetermined amount in the pump plunger 422 to dispense the aspirated serum held in the pipette tip 70 onto a slide 28 in the manner shown in FIG. 7. The spotted slide 28 is thus ready for insertion in the incubator module 14 by the slide engager 250 of the slide transfer device 18.

The aspiration and dispensation operations are repeated for each slide 28 contained within a slide cartridge 24.

After all slides 28 in the slide cartridge 24 have been removed by the slide transfer means 18, the pipette tip ejector 430 will initiate operation. The pinion 382 will thus rotate in a counterclockwise direction as viewed in FIG. 22 to lower the rack 380 and correspondingly lower the frame 334 to a downward limit position permitting interference between the actuator arm 450 and the pin 460 (FIGS. 21 and 22). Such interference causes shifting of the slider 436 to a downward limit position resulting in the pipette tip 70 being pushed off the pump tube end portion 428 by the ejector sleeve 432. The end portion 428 of the pumping tube is thus ready for installation of a new pipette tip 70 in the manner shown in FIGS. 25-27.

Figure 35:
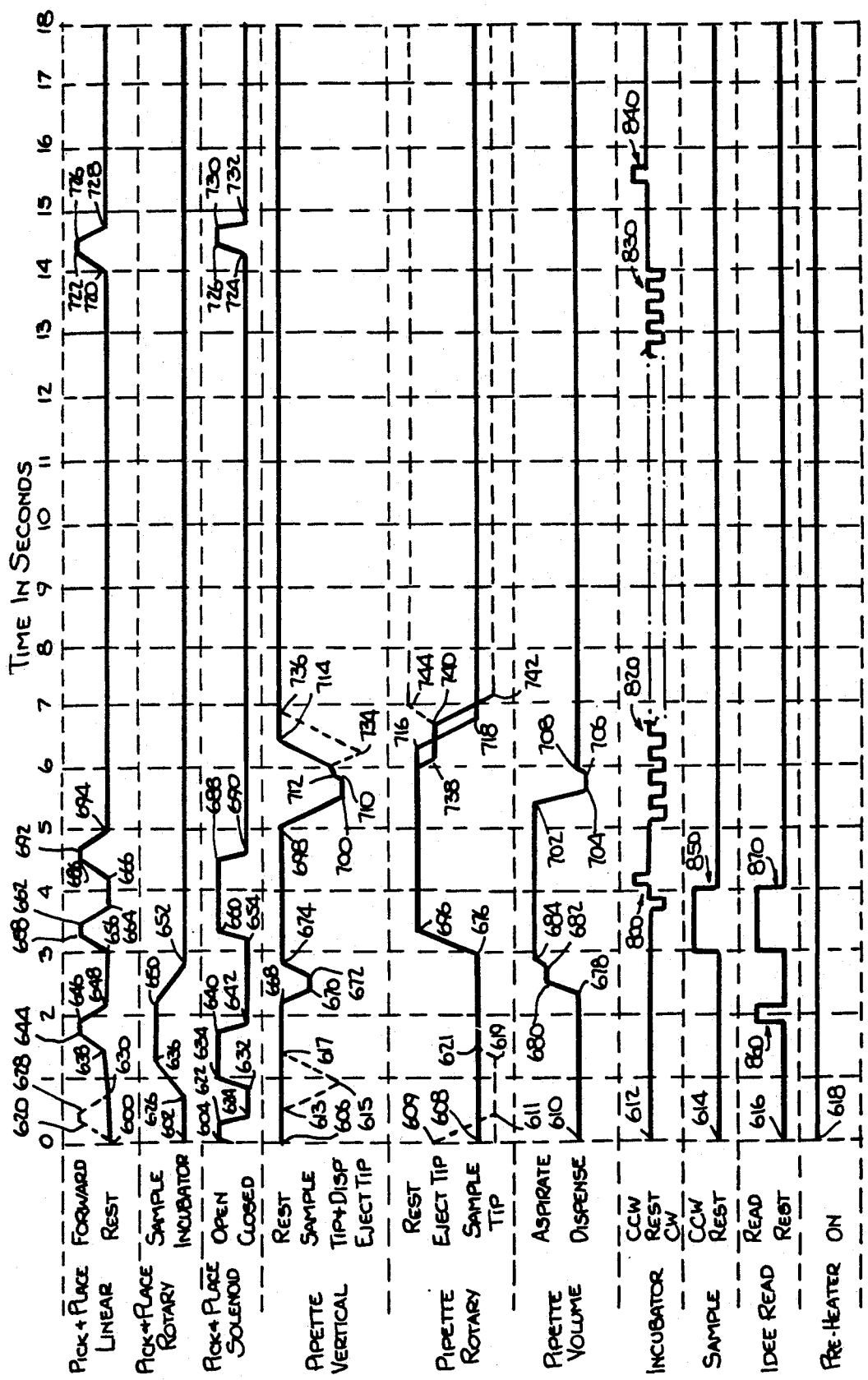
FIG. 35 is a schematic diagram of the sequence of movement of the various components of the slide analysis system; and, FIG. 36 is a simplified schematic block diagram of the electrical functions of the slide analysis system.

An example of the coordination of activity on a time basis in seconds of the slide holding module 12, the incubator module 14, the metering module 16 and the slide transfer means 18 during processing of a slide 28 for analysis is schematically shown in FIG. 35.

In FIG. 35 the activity of the slide transfer means is referred to as:
1. PICK AND PLACE LINEAR
2. PICK AND PLACE ROTARY
3. PICK AND PLACE SOLENOID The activity of the metering module 16 is referred to as:
1. PIPETTE VERTICAL
2. PIPETTE ROTARY
3. PIPETTE VOLUME The activity of the incubator module 14 is referred to as INCUBATOR. The activity of the slide holding module 12 is referred to as SAMPLE. The term SAMPLE is also used in FIG. 35 in reference to a slide 28 in a cartridge 24 held in the slide holding module 12.

The term IDEE READ refers to the bar code reader 130 on the slide holding module 12 and the term PREHEATER refers to the heater 188 in the incubator module 14.

At the start of an operation cycle of the slide analysis system 10, the reference number 600 at PICK AND PLACE LINEAR indicates that the slide engager 250 is in a retracted position, in alignment with the incubator slot 145 in the manner shown in FIG. 2. The reference number 602 at PICK AND PLACE ROTARY indicates that the slide engager 250 is aligned with the incubator slot 145 of the incubator module 14. Reference number 604 at PICK AND PLACE SOLENOID indicates that the slide engaging jaw members 254 and 256 are open in the manner shown in FIG. 14. Thus reference numbers 600, 602 and 604 collectively indicate that the slide engager 250 is aligned with the incubator slot 145 with the slide engager jaw members 254 and 256 in an open position to receive a slide 28.

Reference number 606 at PIPETTE VERTICAL indicates that the metering body 330 is at the rest position of FIG. 20. Reference number 608 at PIPETTE ROTARY indicates that the metering body 330 is aligned with a microcup 68 in a slide cartridge 24 that is held in the slide holding module 24 in the slide analysis position.

Reference number 610 at PIPETTE VOLUME indicates that the pipette plunger 412 is in a fully protracted or dispensed position wherein the pipette tip 70 is without any serum such as shown in FIG. 28.

The reference number 612 at INCUBATOR indicates that the incubator slide holding tray 146 is in a rest position. Reference number 614 at SAMPLE indicates that the turntable 90 in the slide holding module 12 is in a rest position. Reference number 616 at IDEE READ indicates that the bar code reader is not taking a reading. Reference number 618 at PRE-HEATER indicates that the incubator heater 188 is on for the full duration of the slide analysis cycle.

When a transition is made from one cartridge to another, reference number 620 at PICK AND PLACE LINEAR indicates that the slide engager jaws 254 and 256 have moved forward in an open condition into the incubator module 14 to remove a previously analyzed slide 28 from a previously used slide cartridge 24. Reference number 622 at PICK AND PLACE SOLENOID indicates that the slide engager jaws 254 and 256 are starting to close and are fully closed at reference number 624. Reference number 626 at PICK AND PLACE ROTARY indicates that the slide engager 250 remains aligned with the incubator slot 145 during the time that the pick and place solenoid has caused the slide engager jaws 254 and 256 to move from the open position of reference number 622 to the closed position of reference number 624.

Reference numbers 628 and 630 at PICK AND PLACE ROTARY indicate that the slide engager 250 is moving from its protracted position in the incubator module 14 to a retracted position with a withdrawn previously analyzed slide 28. Reference numbers 632 and 634 at PICK AND PLACE SOLENOID indicate that the slide engager jaws 254 and 256 with the previously analyzed slide 28 are opening to permit the slide 28 to drop and be discarded in a container (not shown).

Reference number 636 at PICK AND PLACE ROTARY indicates that the slide engager 250 has been rotated from the incubator module 14 to the microcup 68 in a slide cartridge 24 that is in the slide withdrawal position in the slide holding module 12.

It will be noted that at the start of a new cycle for a new cartridge 24 in the slide withdrawal position, reference number 609 at PIPETTE ROTARY indicates that the metering body 330 has ejected its previously used pipette tip 70 and is moving from the ejection position t the tip installation position indicated by reference number 611 wherein the metering body 330 is in the position shown in FIG. 23. After the metering body 330 has rotated to the tip installation position indicated by reference number 611 at PICK AND PLACE ROTARY, the PIPETTE VERTICAL at reference numbers 613 and 615 indicate that the metering body 330 moves downwardly as shown in FIGS. 25 and 26 to install a new pipette tip 70.

Reference number 617 at PICK AND PLACE VERTICAL indicates that the metering body 330 elevates from the position of FIG. 26 to the position of FIG. 27 after a new pipette tip 70 is installed. During elevation of the metering body 330 from the tip installation position (PIPETTE VERTICAL reference number 615) to the rest position (PIPETTE VERTICAL reference number 617), the metering body is swiveled from the pipette tip holding position in the slide cartridge 24 to the microcup 68. This movement is indicated at reference numbers 619 and 621 of PIPETTE ROTARY.

It will also be noted that the tip installation movement represented by reference numbers 613, 615 and 617 at PIPETTE VERTICAL and reference numbers 609, 611, 619 and 621 at PIPETTE ROTARY occur only once with each new slide cartridge 24 positioned at the slide withdrawal position in the slide holding module 12.

After a new pipette 70 is installed and a first slide 28 has been withdrawn from a slide cartridge 24, the remaining operations relating to all subsequent slides in the same slide cartridge 24, except for the last slide, are identical. Operations with respect to the last slide in the slide cartridge 24 are slightly different and will be separately described.

Thus for all slides 28 subsequent to the first slide 28, reference numbers 600 and 638 at PICK AND PLACE LINEAR indicate gradual protractile movement of the slide engager 250 as PICK AND PLACE ROTARY moves from the INCUBATOR to SAMPLE (or slide holding module 12) as indicated at reference numbers 602, 626 and 636.

Reference number 634 at PICK AND PLACE SOLENOID indicates that the slide engager jaws 254 and 256 remain open while the slide engager 250 is aligned with the external slide withdrawal slot 82 in the slide holding module 12. Reference numbers 640–642 at the PICK AND PLACE SOLENOID indicate that the slide engager jaws 254 and 256 close after reference numbers 644 and 646 are reached at PICK AND PLACE LINEAR, wherein the slide engager jaws 254 and 256 protract through the slide engager withdrawal slot 82 in the slide holding module 12 to grip onto a slide 28 in a slide cartridge 24 that is in the slide withdrawal position.

Reference number 648 at the PICK AND PLACE LINEAR indicates that the slide engager 250 retracts from the slide withdrawal slot 82 in the slide holding module 12 after the slide engager jaws 254 and 256 have been protracted through the slide engager withdrawal slot 82 to grip onto a slide 28 from a slide cartridge 24 that is in the slide withdrawal position.

Reference number 648 at the PICK AND PLACE LINEAR indicates that the slide engager 250 retracts from the slide withdrawal slot 82 in the slide holding module 12 when the slide engager jaws 254 and 256 have closed onto and gripped a slide 28, thus withdrawing a slide 28 from a cartridge 24 in the slide withdrawal position.

Reference numbers 650 and 652 at the PICK AND PLACE ROTARY indicate that the slide engager 250 and the withdrawn slide 28 move from the slide holding module 12 to the incubator module 14 in alignment with the incubator slot 145. Reference number 654 at the PICK AND PLACE SOLENOID indicates that the slide engager jaws 254 and 256 remain closed during movement of the slide engager 250 from the slide holding module to the incubator module.

Reference numbers 656 and 658 at PICK AND PLACE LINEAR indicate that the slide 28 held by the slide engager 250 is inserted into the incubator module 14. Reference number 660 at PICK AND PLACE SOLENOID indicates that the slide engager jaws 254 and 256 open after the slide 28 is inserted in the incubator module 14 to release the slide 28 in the incubator module 14 at a slide retainer station such as station 168 in FIG. 7.

Reference number 662 and 664 at PICK AND PLACE LINEAR indicate that the slide engager 250 retracts from the incubator module 14 and remains retracted to reference number 666 to enable a dry fog reading to be obtained on the slide 28.

Reference numbers 668, 670, 672 and 674 at PIPETTE VERTICAL indicate that the metering head 330 moves from the rest position of FIG. 20 into the microcup 68 per FIGS. 28 and 29 to aspirate serum. The metering head 330 then rises again to the rest position of FIG. 30. Reference number 676 at PIPETTE ROTARY indicates that the metering body 330, during serum aspiration, is aligned with the microcup 68 of the cartridge 24 that is in the slide withdrawal position in the slide holding module 12.

Reference numbers 678, 680, 682 and 684 at PIPETTE VOLUME indicate rising movement of the pump plunger 412 in the metering body 330 to aspirate serum from the microcup 68 into the pipette tip 70 in the manner shown in FIGS. 28-30.

Reference number 686 at PICK AND PLACE LINEAR indicates protraction of the slide engager 250 into the incubator module 14 through the incubator slot 145 to reengage the slide 28 previously left in the incubator module 14 for the dry fog reading. Reference numbers 688 and 690 at PICK AND PLACE SOLENOID indicate that the slide engaging jaws 254 and 256 of the slide engager 250 move from the open position such as shown in FIG. 14 to the closed position such as shown in FIG. 16 to grip the slide 28. Reference numbers 692 and 694 at PICK AND PLACE LINEAR indicate retraction of the slide engager 250 with the withdrawn slide 28 from the incubator module 14 following the dry fog reading.

It will be noted that reference number 652 at PICK AND PLACE ROTARY indicates that the slide engager jaws 254 and 256 remain aligned with the incubator slot 145 during withdrawal of the slide 28 following the dry fog reading.

Reference number 696 at PIPETTE ROTARY indicates that the metering body 330 is swiveled to a rest position in alignment with the slide engager 250 at the incubator slot 145 as shown by the counterclockwise directed arrow in FIG. 2. The angular rest position of the metering body 330, as indicated at reference number 696 of PIPETTE ROTARY is thus in alignment with the incubator slot 145.

Reference numbers 698 and 700 at PIPETTE VERTICAL indicate downward movement of the metering body 330 from the rest position such as shown in FIG. 20 to the dispensing position of FIG. 21. Reference numbers 702 and 704 of PIPETTE VOLUME indicate that the pumping plunger 412 is moved downwardly from the position of FIG. 21 to dispense serum onto the withdrawn slide 28 held by the slide engager 250 as shown in FIG. 7. Reference numbers 706 and 708 at PIPETTE VOLUME indicate that the pump plunger 412 is held in the downward dispensed position until the next new slide 28 to be analyzed is withdrawn from the slide cartridge 24 in the slide holding module 12.

Reference numbers 710, 712 and 714 at PIPETTE VERTICAL indicate gradual vertical movement of the metering body 330 to the rest elevation of FIG. 20 after the serum in the pipette tip 70 has been dispensed onto the slide 28 held by the slide engager 250. Reference numbers 716 and 718 at PIPETTE ROTARY indicate that the metering body 330 is swiveled from the rest position of FIG. 24, indicated by the center line 393, to the sample position indicated by the center line 391 in FIG. 24.

Reference numbers 720 and 722 at PICK AND PLACE LINEAR indicate movement of the slide engager 250 back into the incubator module 14 after the slide 28 has been spotted by the metering body 330. Reference numbers 724 and 726 at PICK AND PLACE SOLENOID indicate that the slide engager jaws 254 and 256 open to release the spotted slide 28 in the incubator module 14 after the slide engager 250 has been protracted through the incubator slot 145.

Reference numbers 726 and 728 at PICK AND PLACE LINEAR indicate retraction of the slide engager 250 from the incubator module 14. Reference numbers 730 and 732 at PICK AND PLACE SOLENOID indicate that the slide engager jaws 254 and 256 are open during such retraction to enable the slide 28 to remain inside the incubator module 14 for slide analysis by the optical head 198 (FIGS. 3 and 31).

Reference numbers 712 and 734 at PIPETTE VERTICAL pertain to the processing of the last slide in a slide cartridge 24. The metering body 330 thus moves vertically downward to the tip eject position of FIG. 22 after the last slide 28 has been spotted in the manner shown in FIG. 21. Reference number 736 at PIPETTE VERTICAL indicates elevation of the metering body 330 to the rest elevation position of FIG. 20, but without the pipette tip 70 as shown in FIG. 25.

Reference numbers 738 and 740 at PIPETTE ROTARY indicate swivel movement of the metering body 330 to an ejection position, intermediate the rest and sample positions of reference numbers 393 and 391 in FIG. 24, for discarding of an ejected pipette tip 70 in a waste bin (not shown). Reference number 744 at PIPETTE ROTARY pertains to swivel movement of the metering head 330 to the rest position corresponding to the reference number 393 in FIG. 24 after the last slide 28 in the last cartridge 24 in the slide holding module 12 has been processed.

Reference number 800 at INCUBATOR indicates the rotation of the incubator slide holding tray 146 that is needed to move an unspotted slide 28 to an optical read station in alignment with the optical head 198 (FIG. 6) for a dry fog reading, and the reverse rotation to move the slide 28 back to the incubator/entry port 145 (FIG. 2) for removal and spotting by the metering module 16.

Reference numbers 820-830 at INCUBATOR indicates the series of 24 incremental rotational steps needed to bring each slide 28 in the incubator 14 to the optical read station in alignment with the optical head 198 (FIG. 6) for a measurement of color development (optical density). Each slide retainer station such as 164-172 (FIG. 2) of the incubator slide holding tray 146 is brought to the optical read station at the optical head 198 regardless of whether a slide 28 is present in a slide retainer station. Also, two of the incubator positions contain grey and white reference standards (not shown) which are read each cycle to provide data for calibrating the instrument.

Reference number 840 at INCUBATOR refers to return of the last read slide back to the incubator entry/exit port 145 (FIG. 2) where it can be removed and discarded. It will be noted that the slide in the reference number 40 position has been in the incubator 14 for the full incubation time.

Reference number 850 at SAMPLE indicates rotation of the turntable 90 (FIG. 2) of the slide holding module 12, if necessary, to find another cartridge 24 with slides 28. This motion occurs only when the cartridge 24 being worked on has been emptied of slides 28.

Reference number 860 at IDEE READ indicates a bar code reading of the slide test type, such as glucose, BUN, etc. The bar code is read as the slide 28 is withdrawn from the cartridge 24 in the slide holding module 12 and passed over the optical scanner 128 (FIG. 3).

Reference number 870 at IDEE READ indicates the reading of the sample identification bar code 62 (FIG. 14) located on each of the cartridges 24. The bar code 62 is read as the turntable 90 in the slide holding module 12 rotates a cartridge 24 past the stationary optical scanner 130 (FIG. 6) also referred to as the IDEE READ STATION.

Figure 36:
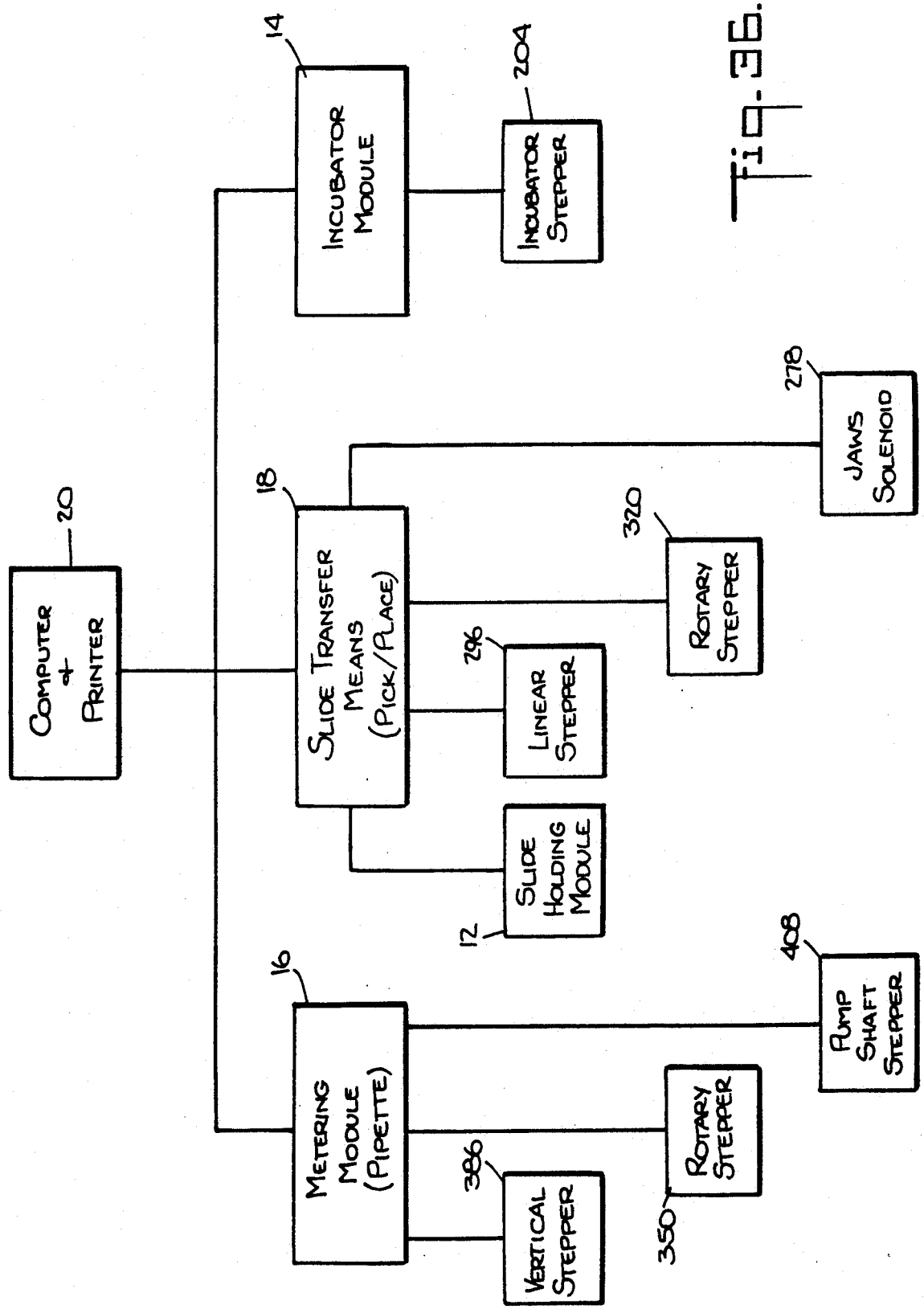

Well known techniques can be used to control the operation of the slide control module 12, the incubator module 14, the metering module 16 and the slide transfer means 18 using a computerized control 20 to obtain the functional operations shown in schematic form in FIG. 36.

Some advantages of the present invention evident from the foregoing description include a slide analysis system that is relatively compact and convenient to use because of a multi-function slide transfer means. Such functions include withdrawal of slides from the slide holding module, placement of the withdrawn slide in an incubator for a dry fog reading, removal of the slide after the dry fog reading has been obtained, holding of the slide for spotting purposes, and insertion of the spotted slide into the incubator for analysis purposes. The slide transfer means also removes the slide from the incubator after the slide analysis has been completed and discards the slide.

The compact nature of the slide analysis system is also due to the multi-function metering or spotting device. The spotting device has a self-contained pipette tip ejector and can swivel from a pipette tip installation position to a sampling position where serum is withdrawn from a microcup to a spotting position wherein serum is dispensed onto a slide to a pipette tip ejection position wherein a used pipette tip is removed and discarded. The functional versatility of the slide transfer mechanism and the metering device as well as the movement and operation of the slide holding module and the incubator module provide a slide analysis system which is convenient for use in a physician's office or any other test area which is of limited space.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A slide analysis system adapted to measure a characteristic of a sample fluid deposited on an analysis slide comprising:

a) slide holding means for holding a plurality of slides to be used in the analysis;

b) incubator means including a a plurality of slide holders, spaced a predetermined distance from said slide holding means;

c) depositing means spaced from said slide holding means and said incubator means for depositing a sample fluid on selected ones of the slides to provide spotted slides;

d) transfer means for withdrawing individual ones of the slides from said slide holding means and for inserting the individually withdrawn slides in said incubator means, said transfer means including:

i) slide engaging means;

ii) means for rotating said slide engaging means to a first predetermined rotational position to align said slide engaging means with one of the slides in said slide holding means, and a second predetermined rotational position to align said slide engaging means with one of said slide holders in said incubator means; and iii) means for displacing said slide engaging means when in said first predetermined rotational position to a first predetermined displaced position at said slide holding means to engage said one of the slides in said slide holding means and for displacing said slide engaging means away from said slide holding means with said one of the slides, and when said slide engaging means is in said second predetermined rotational position to a second predetermined displaced position at said incubator means to insert a slide in said one of said slide holders or remove a slide from said one of said slide holders and for displacing said slide engaging means, with or without a slide, away from said one of said slide holders.

2. The slide analysis system as claimed in claim 1 wherein said slide engaging means includes a pair of elongated gripper members pivoted together to permit pivotal movement toward and away from each other, said gripper members having a first converged position for gripping a slide, and a second diverged position for releasing the grip on the slide.

3. The slide analysis system as claimed in claim 2 further including biasing means cooperable with said gripper members to normally urge said gripper members to said first converted position.

4. The slide analysis system as claimed in claim 2 further including spacer means for causing said gripper to diverge from said first converged position to said second diverged position.

5. The slide analysis system as claimed in claim 1 wherein said slide engaging means includes a pair of separable gripper members for engaging and gripping opposite sides of the slides.

6. The slide analysis system as claimed in claim 5 wherein said slide engaging means include means for converging said gripper members to engage and grip the opposite sides of the slides.

7. The slide analysis system as claimed in claim 6 wherein said slide engaging means further include biasing means cooperating with said gripper members for normally urging said gripper members to converge.

8. The slide analysis system as claimed in claim 5 wherein said gripper members include means for supporting a slide.

9. The slide analysis system as claimed in claim 5 wherein said gripper members include a pair of elongated jaws pivoted together to permit pivotal movement toward and away from each other.

10. The slide analysis system as claimed in claim 1 including means for coordinating the movement of said rotating means and said displacing means such that said rotating means and said displacing means are separately or simultaneously operable.

11. The slide analysis system as claimed in claim 1 wherein said rotating means include means for rotating said slide engaging means to a third predetermined rotational position to permit spotting of a slide held in said slide engaging means.

12. A slide analysis system adapted to measure a characteristic of a sample fluid deposited on an analysis slide comprising:
   a) a slide holding means for holding a plurality of slides to be used in the analysis;
   b) incubator means for the slides, spaced a predetermined distance from said slide holdings means;
   c) depositing means spaced from said slide holding means and said incubator means for depositing sample fluid on selected ones of the slides to provide spotted slides;
   d) transfer means for transferring slides from said slide holding means to said incubator means, said slide holding means and said incubator means located at predetermined angular positions with respect to said transfer means, said transfer means including:
      i) slide engaging means; and
      ii) moving means for rotating said slide engaging means between said predetermined angular positions of said slide holding means and said incubator means; and
      iii) displacing means for displacing said slide engaging means forwardly and rearwardly in the direction defined by said predetermined angular positions.

13. The slide analysis system as claimed in claim 12 including means for coordinating the movement of said moving means and said displacing means such that said moving means and said displacing means are separately or simultaneously operable.

14. The slide analysis system as claimed in claim 12 wherein said moving means include means for rotating said slide engaging means to a third predetermined angular position to permit spotting of a slide held in said slide engaging means.

15. The slide analysis system as claimed in claim 12 wherein said slide engaging means includes a pair of elongated gripper members pivoted together to permit pivotal movement toward and away from each other, said gripper members having a first converged position for gripping a slide, and a second diverged position for releasing the grip on the slide.

16. The slide analysis system as claimed in claim 15 further including biasing means cooperable with said gripping means to normally urge said gripper members to said first converged position.

17. The slide analysis system as claimed in claim 15 further including spacer means for causing said grippers to diverge from said first converged position to said second diverged position.

* * * * *